(12) United States Patent
McQuillen et al.

(10) Patent No.: US 10,309,931 B2
(45) Date of Patent: Jun. 4, 2019

(54) SYSTEMS AND METHODS FOR HUMIDITY DETERMINATION AND USES THEREOF

(71) Applicant: Ford Global Technologies, LLC, Dearborn, MI (US)

(72) Inventors: Michael McQuillen, Warren, MI (US); Daniel A. Makled, Dearborn, MI (US); Gopichandra Surnilla, West Bloomfield, MI (US); Richard E. Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 287 days.

(21) Appl. No.: 15/286,318

(22) Filed: Oct. 5, 2016

(65) Prior Publication Data

US 2018/0095059 A1 Apr. 5, 2018

(51) Int. Cl.
*G01N 29/032* (2006.01)
*G01M 15/10* (2006.01)
(Continued)

(52) U.S. Cl.
CPC ........ *G01N 29/032* (2013.01); *G01M 15/104* (2013.01); *G01N 29/024* (2013.01); *G01N 29/343* (2013.01); *G01N 29/348* (2013.01); *G01S 7/52004* (2013.01); *G01S 7/524* (2013.01); *G01S 7/526* (2013.01); *G01S 15/025* (2013.01); *G01S 15/87* (2013.01); *G01S 15/885* (2013.01); *G01S 15/931* (2013.01); *G01N 2291/015* (2013.01); *G01N 2291/02845* (2013.01); *G01S 7/52006* (2013.01)

(58) Field of Classification Search
CPC .. G01N 29/032; G01N 29/024; G01N 29/343; G01N 29/348; G01S 7/524; G01S 7/526
See application file for complete search history.

(56) References Cited

U.S. PATENT DOCUMENTS

| 4,442,715 A | 4/1984 | Brisken et al. |
| 4,677,595 A | 6/1987 | Obayashi et al. |

(Continued)

OTHER PUBLICATIONS

"Attenuation of Sound Waves," NDT Resource Center, <https://www.nde-ed.org/EducationResources/CommunityCollege/Ultrasonics/Physics/attenuation.htm>, Accessed Nov. 2, 2016, 2 pages.
(Continued)

*Primary Examiner* — David Z Huang
(74) *Attorney, Agent, or Firm* — Julia Voutyras; McCoy Russell LLP

(57) ABSTRACT

Methods and systems are provided for conducting measurements of relative humidity via the use of either an ultrasonic sensor positioned on the vehicle, or via another sensor. In one example, responsive to a request for a relative humidity measurement and an indication of fueled engine operation, the ultrasonic sensor may be utilized, whereas responsive to an indication of non-fueled engine operation, another sensor may be utilized. In this way, robust measurement of relative humidity with desired accuracy may be actively determined, rather than opportunistically, and such measurements of relative humidity may be utilized to adjust vehicle operating parameters, which may improve overall vehicle operation.

16 Claims, 15 Drawing Sheets

(51) Int. Cl.

| | |
|---|---|
| *G01N 29/024* | (2006.01) |
| *G01N 29/34* | (2006.01) |
| *G01S 15/93* | (2006.01) |
| *G01S 15/02* | (2006.01) |
| *G01S 7/52* | (2006.01) |
| *G01S 7/524* | (2006.01) |
| *G01S 7/526* | (2006.01) |
| *G01S 15/87* | (2006.01) |
| *G01S 15/88* | (2006.01) |

(56) References Cited

U.S. PATENT DOCUMENTS

| | | | |
|---|---|---|---|
| 5,549,111 | A | 8/1996 | Wright et al. |
| 7,540,194 | B2 | 6/2009 | Sugiura et al. |
| 7,607,352 | B2 | 10/2009 | Endou |
| 7,715,976 | B1 * | 5/2010 | Xiao ............ F02M 26/46 123/406.48 |
| 8,166,824 | B2 | 5/2012 | Sugiura et al. |
| 2006/0196272 | A1 | 9/2006 | Sugiura et al. |
| 2010/0028722 | A1 | 2/2010 | Knoop |
| 2012/0023910 | A1 | 2/2012 | Parrish et al. |
| 2014/0202426 | A1 | 7/2014 | Surnilla et al. |
| 2014/0250864 | A1 | 9/2014 | Heinecke et al. |
| 2014/0300504 | A1 | 10/2014 | Shaffer et al. |
| 2016/0115883 | A1 * | 4/2016 | Mischler ............ F02D 41/0072 123/703 |

OTHER PUBLICATIONS

Bacon, D.R., et al., "Acoustics: The Speed and Attenuation of Sound," Kaye and Laby Tables of Physical and Chemical Constants, NPL National Physics Laboratory, <http://www.kayelaby.npl.co.uk/general_physics/2_4/2_4_1.html>, Accessed Nov. 2, 2016, 8 pages.

Harris, Cyril M., "Absorption of Sound in Air Versus Humidity and Temperature," The Journal of the Acoustical Society of America, vol. 40, pp. 148-159, 1996, 12 pages.

Jakevicius, L., et al., "Ultrasound Attenuation Dependence on Air Temperature in Closed Chambers," Ultragardas Journal vol. 63.1, pp. 18-22, 2008, 5 pages.

Motegi, Takahiro, et al., Abstract from "Humidity Measurement Using a Ultrasonic Probe Based on Sound Attenuation," The Journal of the Acoustical Society of America, 2012, AIP Scitation, <http://scitation.aip.org/content/asa/journal/asa/131/4/10.1121/1.4709336>, Accessed Nov. 2, 2016, 2 pages.

Motegi, Takahiro, et al., "Measurement of Humidity Based on Sound Attenuation," Proceedings of Symposium on Ultrasonic Electronics vol. 32, pp. 199-200, 2011, <http://www.use-jp.org/proceedings/USE11/pdf/2Pb2-5.pdf>, Accessed Nov. 2, 2016, 2 pages.

Motegi, Takahiro, et al., Abstract from "Simultaneous Measurement of Air Temperature and Humidity Based on Sound Velocity and Attenuation Using Ultrasonic Probe," Japanese Journal of Applied Physics vol. 52.7, 2013, <http://iopscience.iop.org/1347-4065/52/7S/07HC05/pdf/1347-4065_52_7S_07HC05.pdf>, Accessed Nov. 2, 2016, 3 pages.

"About Ultrasonics," Migatron Corp., <http://www.migatron.com/understanding-ultrasonic-technology/>, Accessed Nov. 2, 2016, 5 pages.

Vladisauskas, A., et al., "Absorption of Ultrasonic Waves in Air," Ultragarsas Journal, 2004, pp. 46-49, <http://www.ktu_.lt/ultraljournal/pdf_50_1/50/2004-Vol.1_09-A_Vladisauskas.pdf>, Accessed Nov. 2, 2016, 4 pages.

McQuillen, Michael, et al., "Systems and Methods for Humidity Determination and Uses Thereof," U.S. Appl. No. 15/286,211, filed Oct. 5, 2016, 115 pages.

McQuillen, Michael, et al., "Systems and Methods for Humidity Determination and Uses Thereof," U.S. Appl. No. 15/286,277, filed Oct. 5, 2016, 117 pages.

* cited by examiner

| Desired operational use | Ultrasonic frequency |
|---|---|
| Short Range | All frequency ranges can be used. Choose optimal frequency that the piezoelectric crystal was designed to operate at. |
| Medium Range | Low to middle frequency to reduce attentuation. |
| Long Range | Low frequency operation to minimize attenuation and maximize sensing distance |

FIG. 13

SYSTEMS AND METHODS FOR HUMIDITY DETERMINATION AND USES THEREOF

FIELD

The present description relates generally to methods and systems for determining relative humidity via ultrasonic sensors or other means, and based on the humidity determination, adjusting one or more vehicle operating parameters.

BACKGROUND/SUMMARY

One or more ultrasonic sensors may be mounted on an automotive vehicle, for example a hybrid electric vehicle (HEV), enabling a distance determination between the sensor and an external object. Such an ultrasonic sensor may consist of at least a piezoelectric disc and a membrane, configured to convert electrical energy into mechanical energy, and mechanical energy into electrical energy. More specifically, an oscillated voltage may be applied to the piezo disc such that the piezo disc and membrane vibrate and generate ultrasonic waves at a frequency based on the frequency of voltage oscillation. After the waves are emitted, sensors wait for echoes to come back from objects, and when the echoes interact with the sensor/membrane, the membrane is excited to vibrate. The piezo disc attached to the membrane converts the vibration to voltage, and based on the timeframe of sending and receiving the ultrasonic wave, a distance determination to an object may be inferred.

In a vehicle, ultrasonic sensors may be utilized for inferring distance between a vehicle and obstacles during either assisted, or fully automated parking, for example. However, there are a number of factors that may affect optimal operation of an ultrasonic sensor. Such factors may include temperature, humidity, target surface angle, and reflective surface roughness. Of these four variables, determining humidity in a vehicle may be complicated, particularly in a case where a vehicle may not include a dedicated humidity sensor. Furthermore, estimation of ambient humidity is important for a number of engine operating parameters, such as an amount of exhaust gas recirculation (EGR), spark timing, combustion air-fuel ratio, etc.

Various kinds of sensors may be used to estimate the ambient humidity. As one example, oxygen sensors, such as a Universal Exhaust Gas Oxygen (UEGO) sensor used for exhaust air-fuel ratio control, may be used for ambient humidity estimation under selected conditions. Such oxygen sensors can be located in an exhaust passage or an intake air passage. In one example, shown by Surnilla et al. in US 20140202426, an exhaust gas oxygen sensor coupled to an engine bank may be utilized to opportunistically determine ambient humidity during conditions when the bank is selectively deactivated, and while the other bank continues to combust. A variable voltage may be applied to the sensor, and a change in pumping current may be correlated with the ambient humidity.

However, the inventors herein have recognized potential issues with such a system. As one example, humidity measurements may be non-specific, where humidity is estimated either opportunistically when possible, or when desired. For example, conditions may not always be present for conducting a humidity measurement via an exhaust gas oxygen sensor. Still further, where an exhaust oxygen sensor is used for humidity sensing, frequent application of a variable voltage may result in sensor blackening, and eventual degradation. Thus, for accurate and timely humidity measurements, an ability to selectively utilize one method of humidity measurement over another may be desirable, and may improve vehicle operating conditions that take humidity into account.

The inventors herein have identified an approach by which the issue described above may be at least partially addressed. In one example, a method is provided, comprising indicating relative humidity from differences between pairs of reflected signals from a single ultrasonic sensor coupled to a vehicle, each of the reflected signals having substantially equivalent transit time from an object back to the ultrasonic sensor; indicating relative humidity from one or more sensors coupled to the vehicle other than the ultrasonic sensor; and selecting which relative humidity indication method to use in response to environmental or vehicle operating conditions.

As an example, exhaust gas constituents may be detected from a gas sensor coupled to an exhaust of an engine which propels the vehicle, and during non-fueled operation of the engine, relative humidity may be indicated from the gas sensor. Where either the ultrasonic sensor or the gas sensor is utilized to conduct a relative humidity estimation, the method may include updating a previous humidity indication with the selected humidity indication.

As another example, vehicle operating conditions may be adjusted responsive to the relative humidity indication. For example, the method may include propelling the vehicle at least in part by the engine, where the engine includes an intake manifold and an exhaust manifold, and where the engine operates by combustion of fuel provided to the engine; controlling an amount of exhaust gas recirculated to the intake manifold of the engine while the engine is operating; and wherein adjusting vehicle operating conditions responsive to indicating relative humidity includes one of at least an amount of the exhaust gas recirculation, and an amount by which ignition timing of spark provided to the fuel for combustion is retarded or advanced. In this way, a humidity determination may be conducted via a suitable sensor, for example either a gas sensor or an ultrasonic sensor. The humidity determination may be conducted under conditions when a humidity determination is requested, for example responsive to an indicated change in ambient temperature greater than an ambient temperature threshold, a change in ambient pressure greater than an ambient pressure threshold, a threshold time of engine operation exceeding an engine operation time threshold, and a distance of vehicle travel greater than a distance threshold. By conducting a humidity determination via a suitable sensor, and adjusting engine operation based on the humidity determination, vehicle operating conditions may be improved, where said vehicle operating conditions may be based, at least in part on, a determination of relative humidity.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 13 depicts an example lookup table that may be used in conjunction with the method of FIG. 12, for selecting optimal ultrasonic frequency(s) for distance measurements, based on adjusted distance detection thresholds.

DETAILED DESCRIPTION

Figure 2:
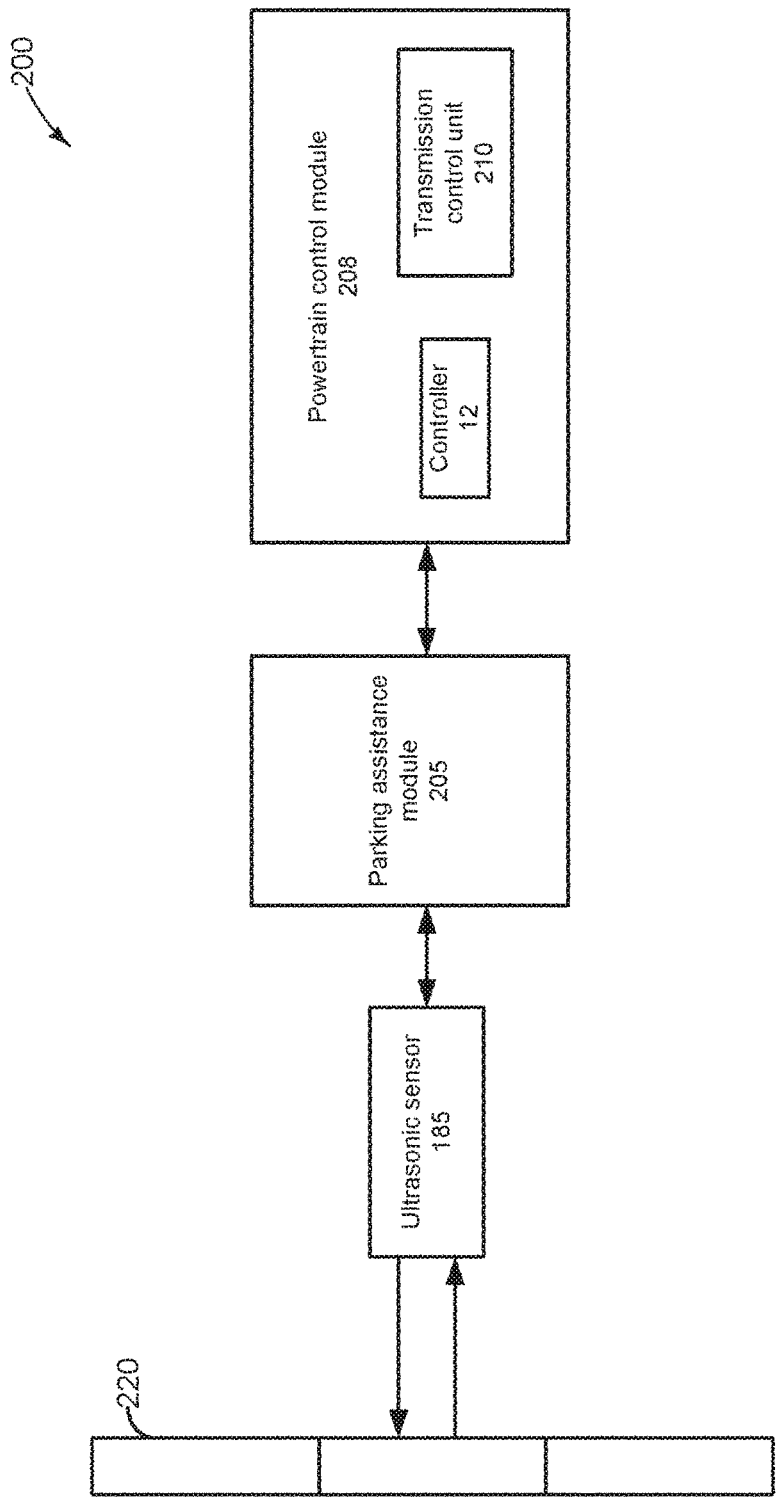
FIG. 2 shows a block diagram of components of a vehicle system that uses ultrasonic sensor(s) for assisting or controlling vehicle parking maneuvers.
Figure 3A:
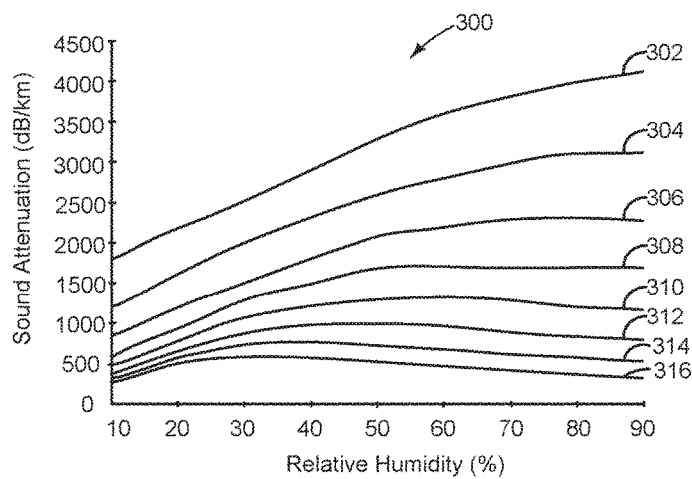
FIG. 3A depicts a graph detailing effects of humidity and ultrasonic frequency on sound attenuation.

The following description relates to systems and methods for conducting relative humidity measurements and adjusting vehicle operation parameters responsive to the relative humidity determination. Such measurements may be carried out by a vehicle system including an internal combustion engine, where the vehicle may further be configured with one or more onboard camera(s) and one or more ultrasonic sensor(s), such as the vehicle system depicted in FIG. 1. In some examples, the vehicle may be a hybrid vehicle that can operate for extended time periods without operation of the engine. Knowledge of relative humidity may improve functions such as assisted or fully-automated parking procedures, where the procedures may be enabled via a parking assist system as illustrated in FIG. 2. In some examples, humidity measurements may be determined via an ultrasonic sensor, based on a relationship between sound attenuation, relative humidity, and ultrasonic frequency, as illustrated in FIG. 3A. For example, a difference in sound attenuation for a given pair of frequencies may enable an estimation of ambient humidity, indicated by FIG. 3B. Such an estimation may be conducted via a transfer function, graphically depicted in FIG. 3C.

Figure 4:
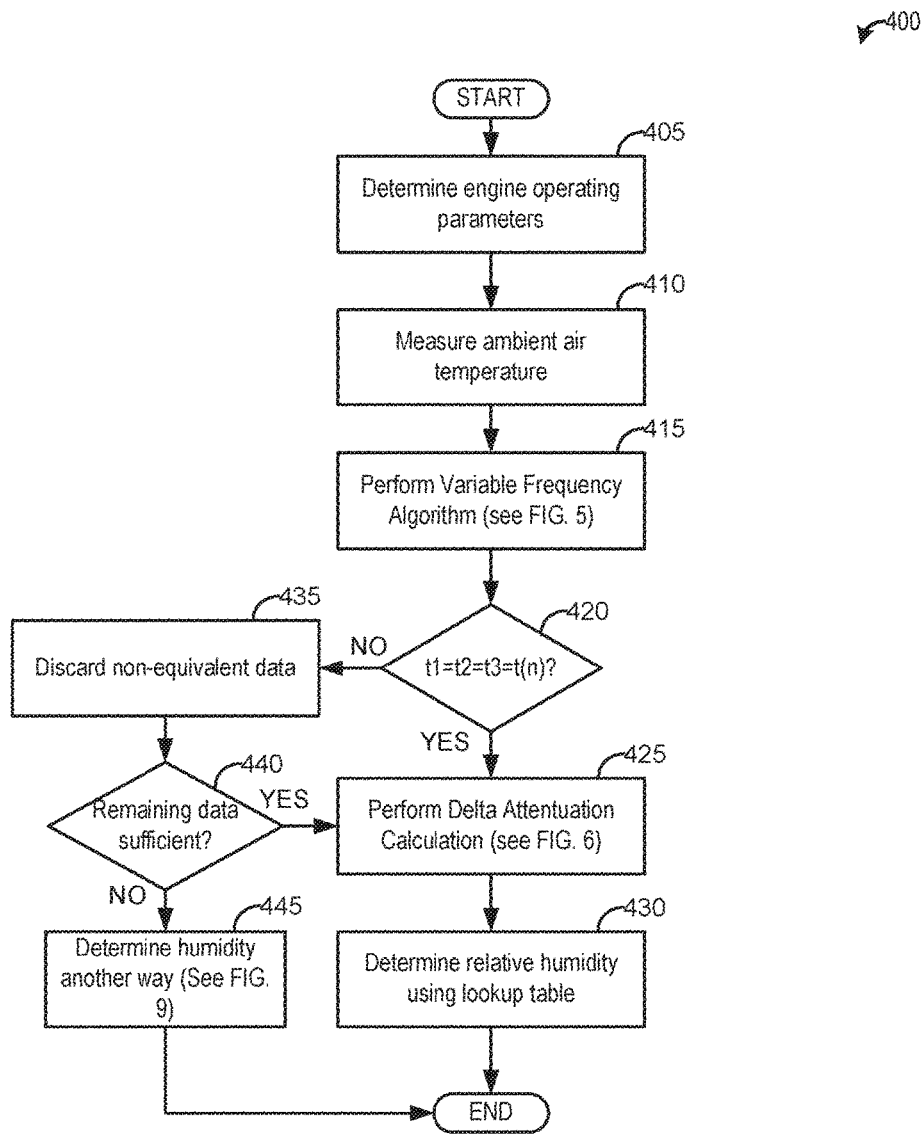
FIG. 4 shows a high level example method for conducting a relative humidity determination via the use of an ultrasonic sensor.
Figure 5:
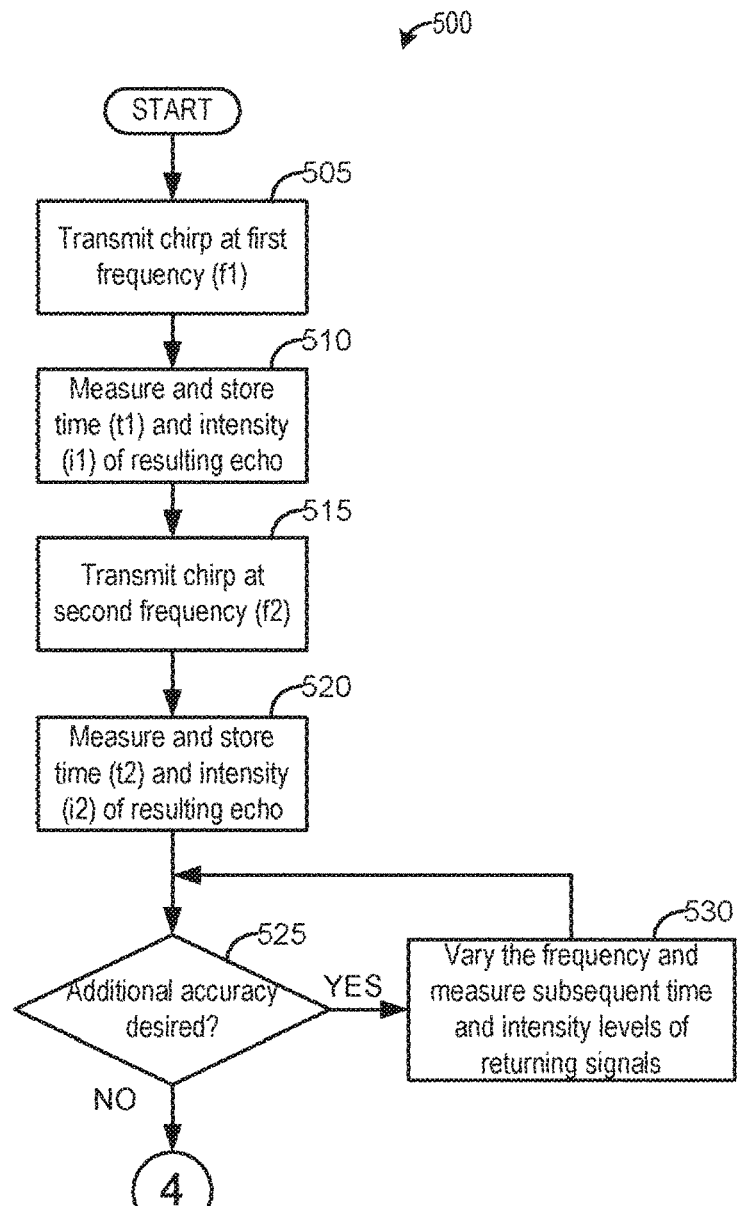
FIG. 5 shows a high level example method for conducting a variable frequency algorithm used by an ultrasonic sensor, as a sub-method of FIG. 4.
Figure 6:
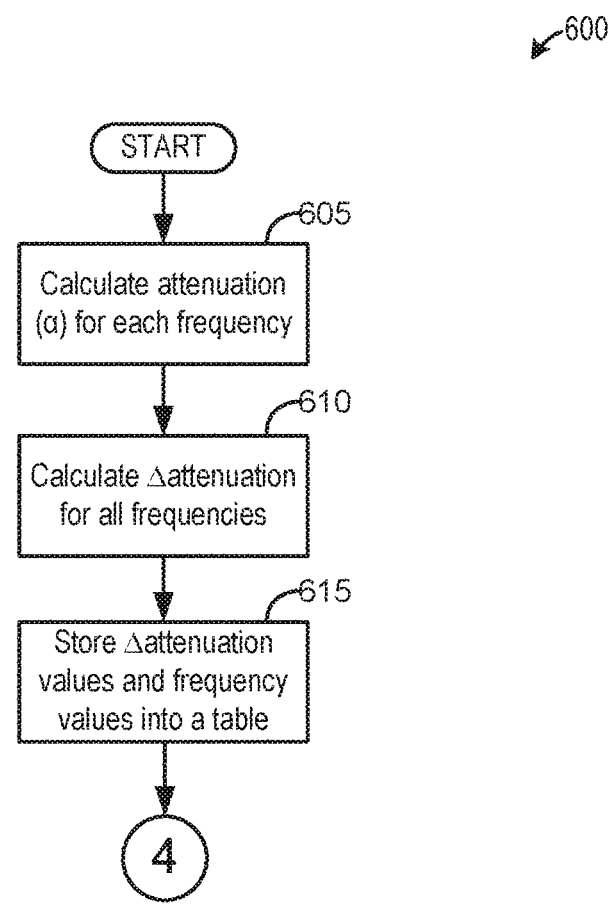
FIG. 6 shows a high level example method for conducting a delta attenuation calculation, as a sub-method of FIG. 4.

FIG. 4 illustrates a high level example method for conducting a humidity measurement via the use of an ultrasonic sensor. As a sub-method of FIG. 4, a variable frequency algorithm as depicted in FIG. 5 may be used to determine sound attenuation for two or more ultrasonic frequency(s), which may then enable a delta attenuation calculation, as depicted in FIG. 6. By conducting the variable frequency algorithm and the delta attenuation calculation, a relative humidity measurement may be determined.

Figure 7:
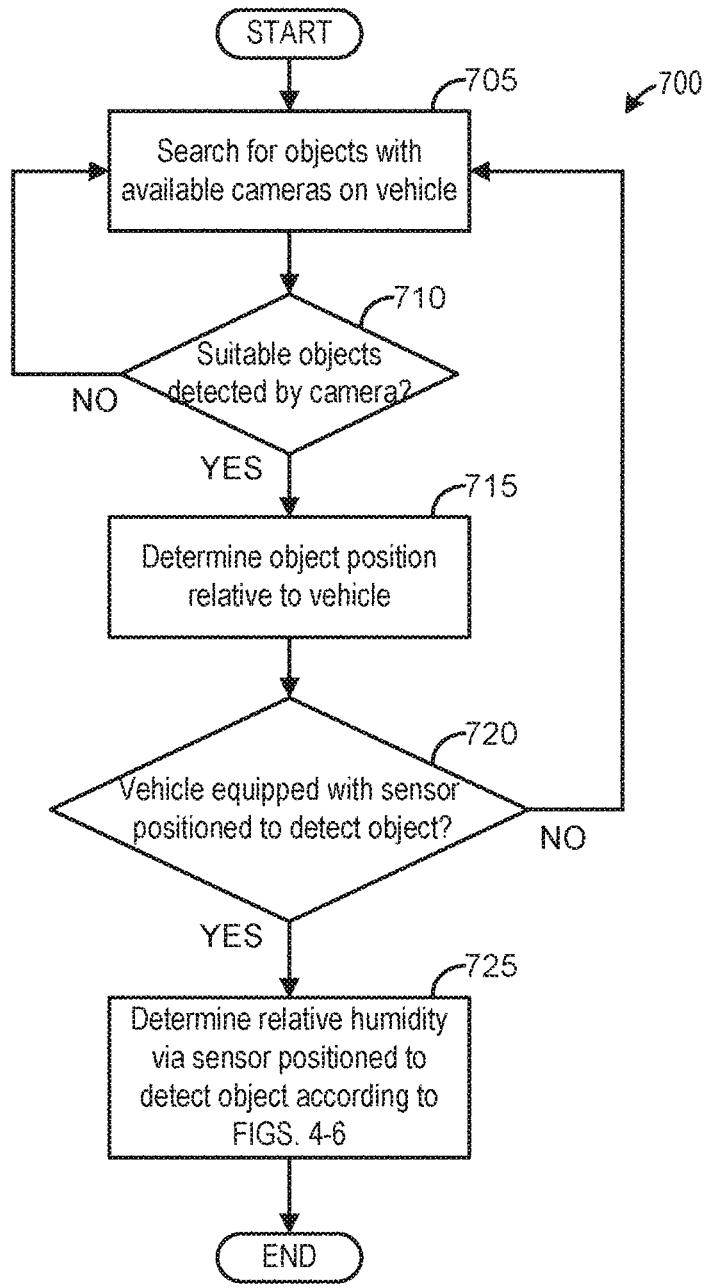
FIG. 7 shows a high level example method for using one or more onboard camera(s) for selecting an appropriate ultrasonic sensor for conducting a relative humidity measurement.

In some examples, one or more onboard camera(s) may be utilized to identify suitable objects of interest for conducting the humidity determination procedure via the use of an ultrasonic sensor. Accordingly, a method for detecting suitable objects via the use of one or more camera(s) is illustrated in FIG. 7.

Figure 8:
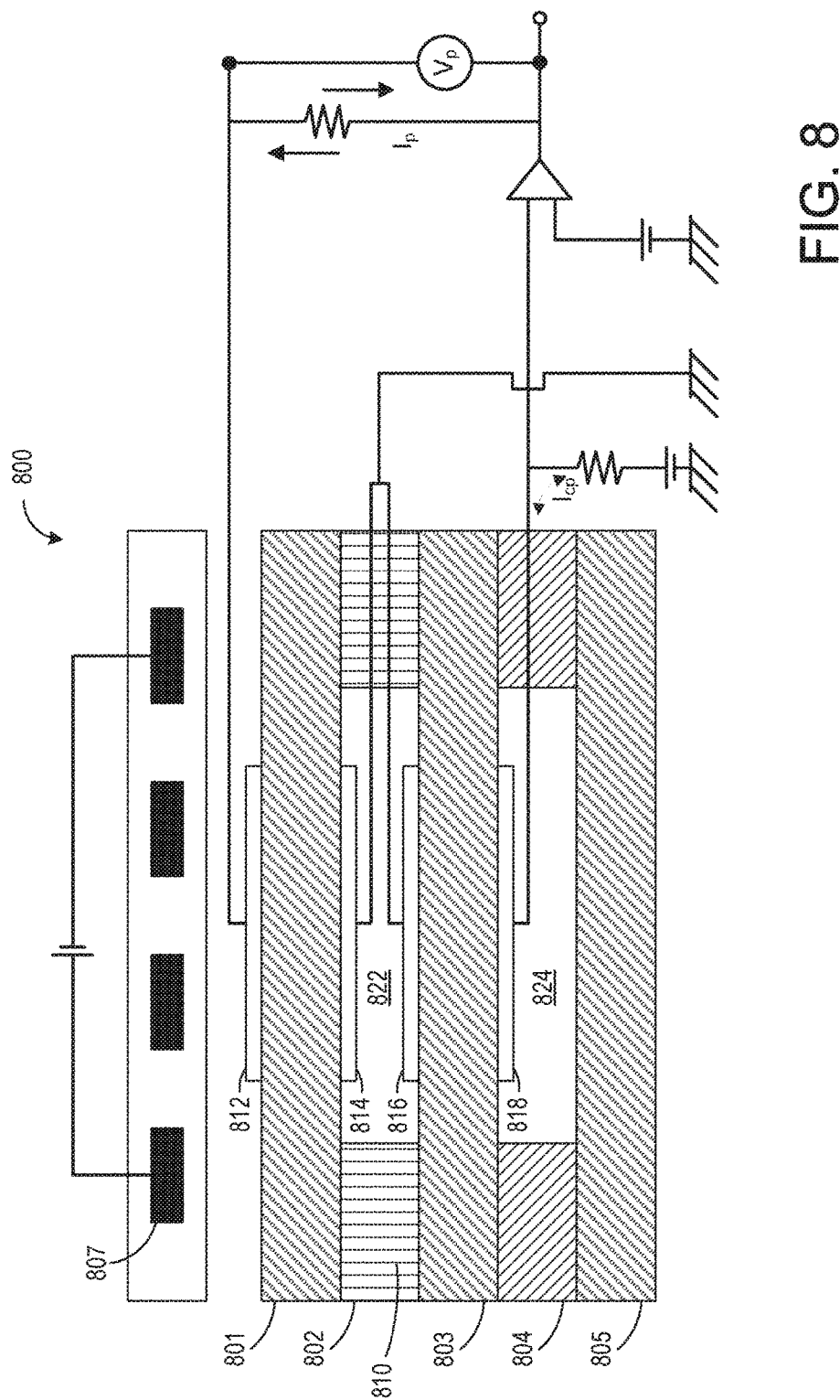
FIG. 8 shows a schematic diagram of an example UEGO sensor.
Figure 9:
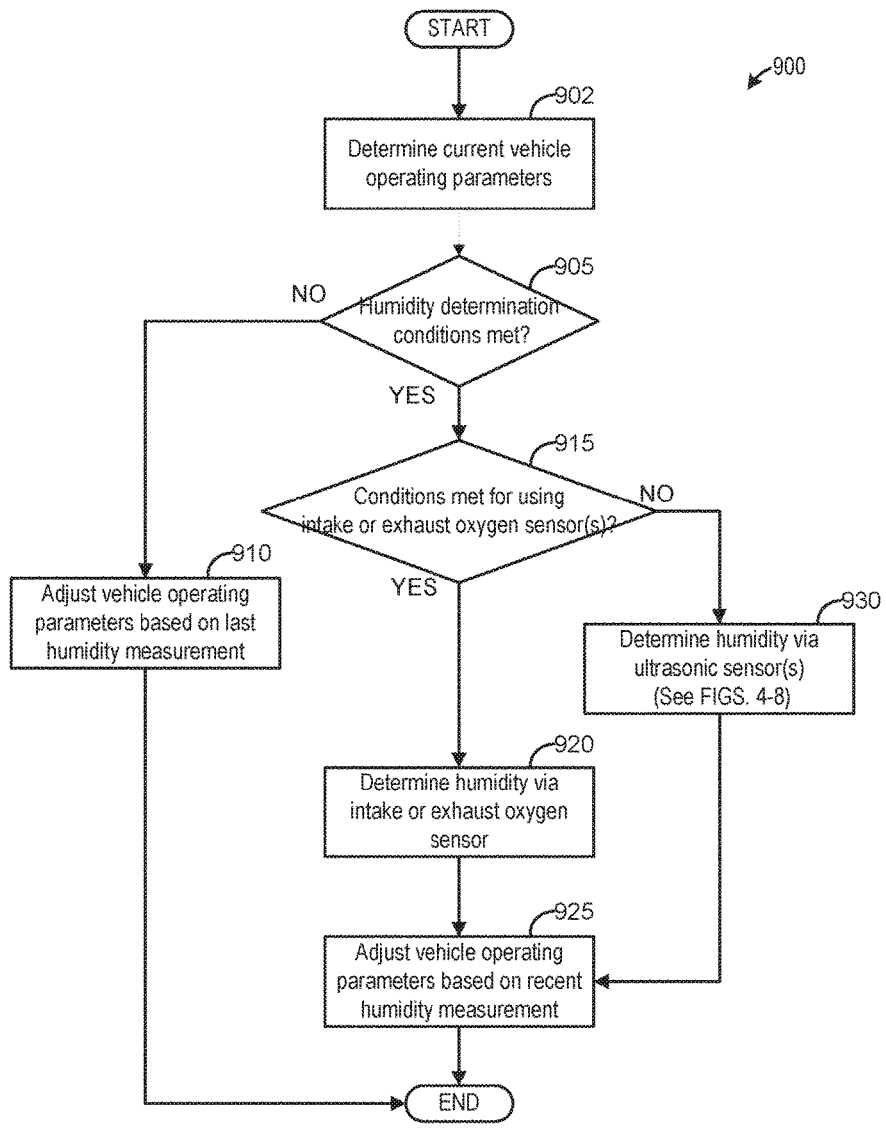
FIG. 9 shows a high level example method for opportunistically conducting a humidity measurement using either an oxygen sensor or an ultrasonic sensor, responsive to environmental or vehicle operating conditions.

In further examples, some conditions may not be optimal for enabling a humidity determination via an ultrasonic sensor, and another means may be desirable, and vice versa. For example, an oxygen sensor positioned in an intake or exhaust manifold of a vehicle engine may be used in lieu of an ultrasonic sensor to indicate humidity under particular vehicle operation conditions. Such an example of an oxygen sensor is illustrated in FIG. 8, and an example method for selecting whether to conduct a humidity measurement via an oxygen sensor or an ultrasonic sensor, based on vehicle operating conditions, is illustrated in FIG. 9.

Figure 1:
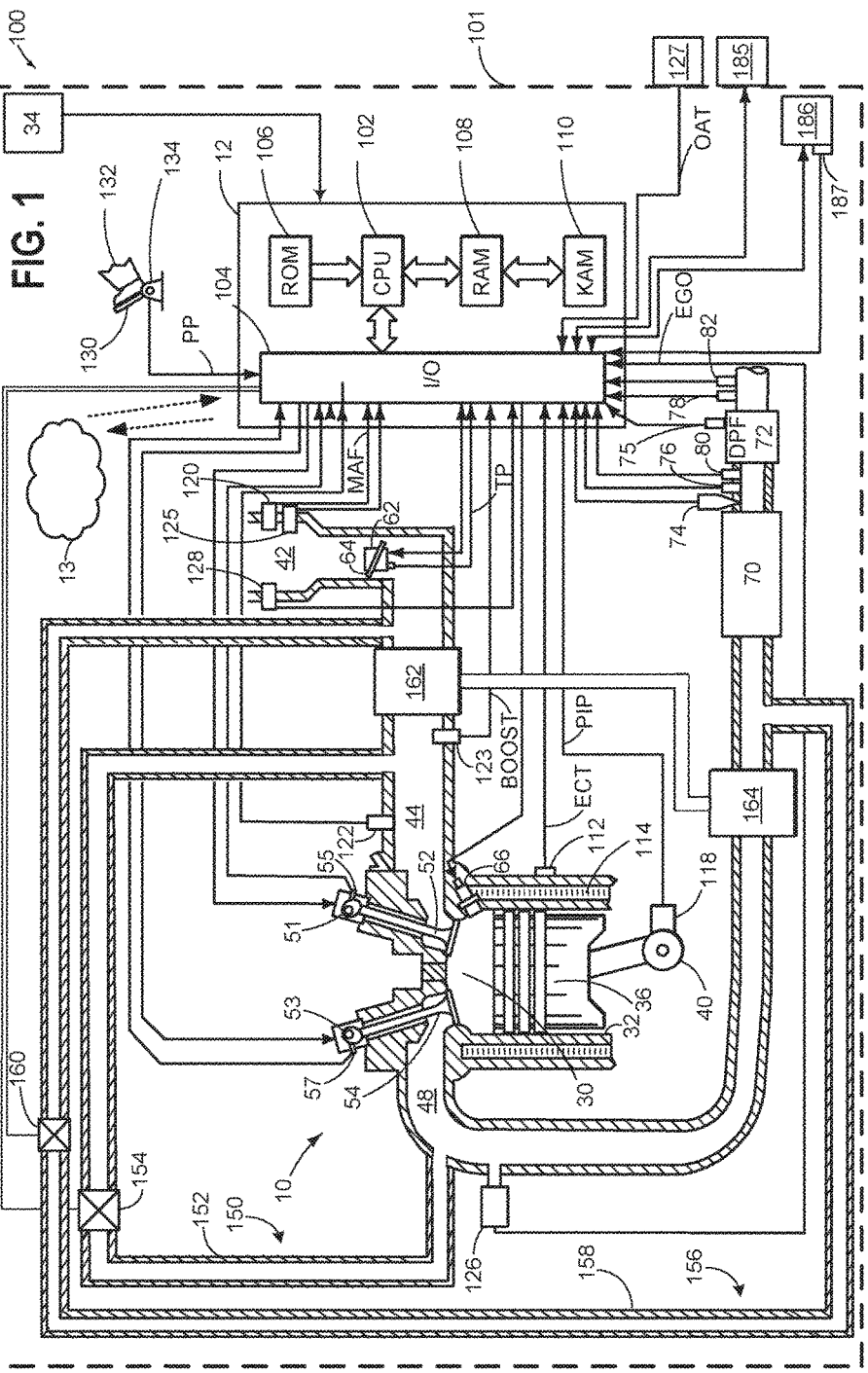
FIG. 1 shows a schematic depiction of an internal combustion engine.

The vehicle system depicted in FIG. 1 may in some examples comprise a diesel engine, and may thus include a diesel particulate filter (DPF) for capturing and storing soot from the engine. Regeneration of such a filter may include high exhaust temperatures, and thus it may be desirable in some examples to indicate whether an object is within a proximity of the exhaust prior to conducting the regeneration procedure. Furthermore, distance thresholds for the object may in some examples be adjusted as a function of relative humidity and temperature in a location near the exhaust. For example, thermal conductivity of air may vary as a function of humidity and temperature, indicated by the graph depicted in FIG. 10. Accordingly, a distance threshold for an object may in some examples be adjusted, based on an inferred thermal conductivity of air, as illustrated in the method depicted in FIG. 11. By adjusting a distance threshold, DPF regeneration procedures may be enable to execute more frequently, for example.

As discussed above, humidity may comprise a noise factor for operational use of an ultrasonic sensor. Thus, in some examples, knowledge of ambient humidity may improve operational use of the ultrasonic sensor. In one example, a distance detection threshold may be adjusted, according to the method illustrated in FIG. 12. As an example, adjusting the distance detection threshold may include indicating suitable frequencies for conducting a distance measurement using an ultrasonic sensor. In such an example, a lookup table, such as the lookup table illustrated in FIG. 13 may be used in conjunction with the method illustrated in FIG. 12, in order to determine an optimal frequency for a desired operational use of the ultrasonic sensor.

Figure 14:
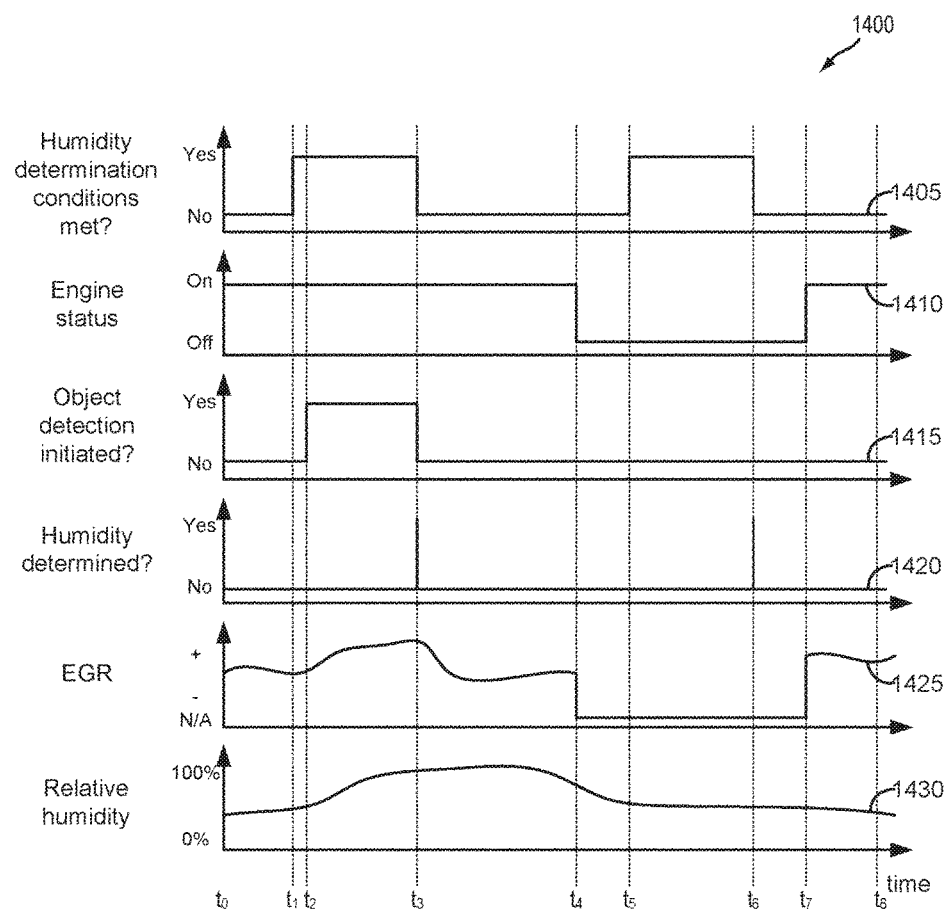
FIG. 14 shows an example timeline for conducting a humidity determination procedure based on vehicle operating conditions.
Figure 15:
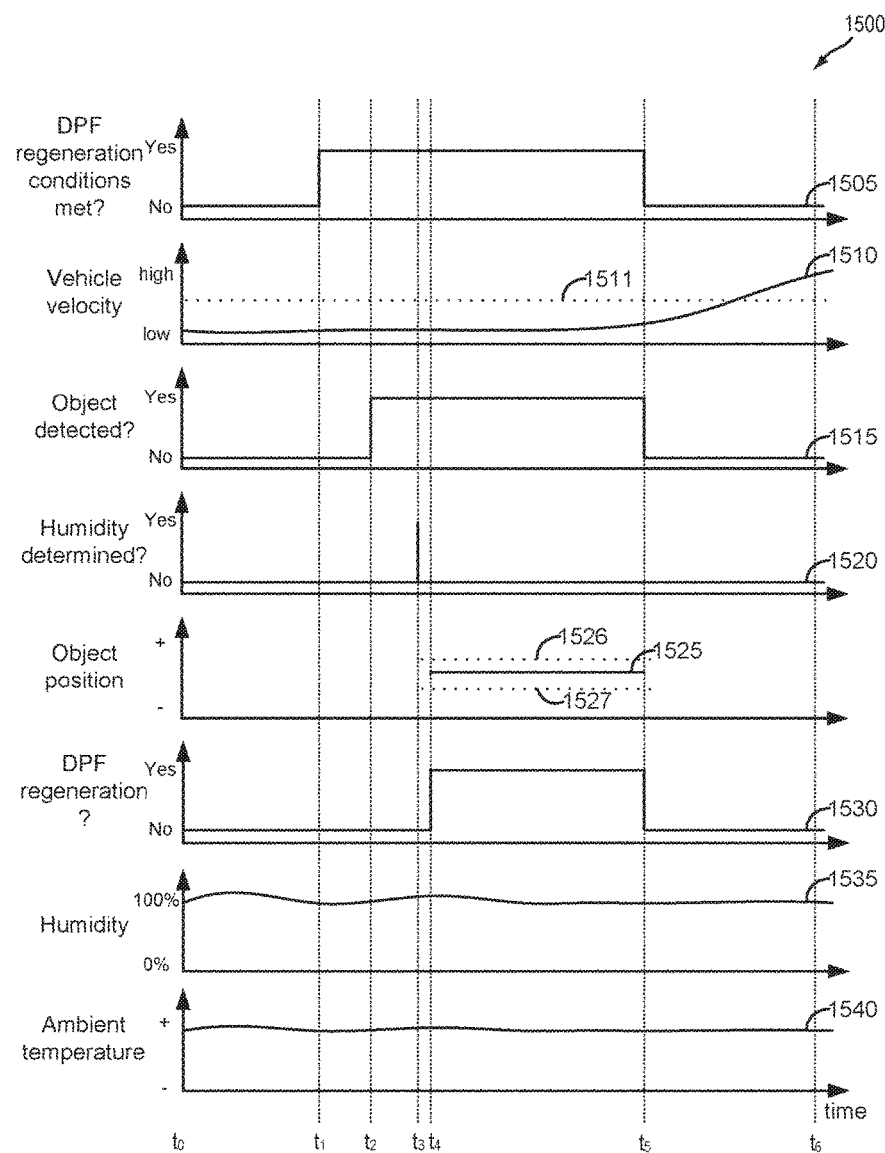
FIG. 15 shows an example timeline for conducting a DPF regeneration event, where conditions of the regeneration event may be at least partially based on an indication of ambient humidity.

Example timelines for selecting humidity determination methodology based on vehicle operating procedures, and for conducting a DPF regeneration procedure based at least in part on a humidity determination, are illustrated in FIG. 14, and FIG. 15, respectively.

FIG. 1 is a schematic diagram showing one cylinder of a multi-cylinder engine 10 in an engine system 100. The engine system 100, may be coupled inside a propulsion system of an on road vehicle system 101. An outside air temperature (OAT) sensor 127 may be positioned on the exterior of the vehicle system 101. The OAT sensor may estimate the ambient air temperature that may be used for engine operations and in addition, OAT sensor 127 may be used in some examples to trigger humidity measurements corresponding to a change in ambient temperature. In some examples, one or more camera(s) 186 may be positioned at one or more positions (e.g. locations) on the vehicle, and may be configured to obtain images including, but not limited to, an environment around the vehicle. In some examples, one or more camera sensor(s) (e.g. 187) may be configured to provide positional information regarding the one or more camera(s) 186. For example, if a camera is rotatable, camera sensor(s) 187 may convey a direction that the camera is facing to a vehicle controller (e.g. 12). In other examples, where the camera is not rotatable, camera sensor(s) 187 may still be configured to indicate position and a direction the camera is facing. Furthermore, one or more ultrasonic sensor(s) 185 may be positioned at one or more positions on the vehicle, and may be configured to measure distance from the ultrasonic sensor(s) and an object of interest. For example, the ultrasonic sensor may be configured to transmit and receive signals in the form of sound waves. In some examples, an object of interest may be detected by the ultrasonic sensor(s) themselves. In other examples, the one or more camera(s) may detect an object of interest, whereupon the ultrasonic sensor(s) may be utilized to conduct a distance measurement between the ultrasonic sensor(s) and the object of interest. In still further examples, as will be discussed in detail further below, the ultrasonic sensor(s) may be utilized to obtain relative humidity measurements. For example, certain conditions may trigger a request for a relative humidity measurement, where the certain conditions may include a change in temperature greater than a predetermined temperature threshold, an ambient pressure change greater than an ambient pressure threshold, a threshold of time of engine operation or distance of vehicle travel greater than a threshold distance since a previous (e.g. last) humidity measurement.

More specifically, as will be described further below, in some examples ultrasonic sensor 185 may be utilized to obtain distance proximity measurements between a vehicle and object(s) of interest (e.g. obstacles) during a vehicle operation such as an assisted or fully-automated parking maneuver. However, a noise factor for the ultrasonic sensor(s) 185 may be humidity. Thus, in some examples, knowledge of relative humidity may be used to adjust a detection threshold of the ultrasonic sensor, which may involve indicating suitable frequencies for conducting distance measurements using the ultrasonic sensor. In still further examples, knowledge of relative humidity may improve engine operating conditions where such conditions rely on an accurate estimation of relative humidity, as will be discussed further below.

Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include fixed cam timing, or may include one or more cams and may utilize one or more of cam profile switching (CPS), variable cam timing (VCT), variable valve timing (VVT) and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown coupled directly to combustion chamber 30 for injecting fuel. In this manner, fuel injector 66 provides what is known as direct injection of fuel into combustion chamber 30. The fuel injector may be mounted in the side of the combustion chamber or in the top of the combustion chamber, for example. Fuel may be delivered to fuel injector 66 by a fuel system (not shown) including a fuel tank, a fuel pump, and a fuel rail, which may be a common fuel rail.

Intake manifold 44 may include a throttle 62 having a throttle plate 64. However, in other examples, the throttle may be located in intake passage 42. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air and/or EGR provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

In some examples, engine 10 may further include a compression device such as a turbocharger or supercharger including at least a compressor 162 arranged along intake manifold 44. For a turbocharger, compressor 162 may be at least partially driven by a turbine 164 (e.g., via a shaft) arranged along exhaust passage 48. For a supercharger, compressor 162 may be at least partially driven by the engine and/or an electric machine, and may not include a turbine. Thus, the amount of compression (e.g., boost) provided to one or more cylinders of the engine via a turbocharger or supercharger may be varied by controller 12.

Further, a sensor 123 may be disposed in intake manifold 44 for providing a BOOST signal to controller 12.

Engine 10 may further include a high pressure EGR system 150. High pressure EGR system 150 may include an EGR conduit 152 coupled to the exhaust 48 upstream of turbine 164 and coupled to the intake 44 downstream of compressor 162. High pressure EGR system 150 may include an EGR valve 154 disposed along EGR conduit 152 to control exhaust flow through EGR system 150. Engine 10 may also include a low pressure EGR system 156. Low pressure EGR system 156 includes an EGR conduit 158 coupled to the exhaust 48 downstream of turbine 164 and coupled to the intake 44 upstream of compressor 162. Low pressure EGR system 156 may include an EGR valve 160 disposed along EGR conduit 152 to control exhaust flow through EGR system 156.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Further sensors may include camera sensors 187, ultrasonic sensors 185, OAT sensor 127, etc.

Storage medium read-only memory 106 can be programmed with computer readable data representing instructions executable by processor 102 for performing the methods and control strategies described below as well as other variants that are anticipated but not specifically listed.

In addition, controller 12 may receive data from an onboard navigation system 34 (e.g. a Global Positioning System (GPS)) that an operator of the vehicle may interact with. The navigation system 34 may include one or more location sensors for assisting in estimating vehicle speed, vehicle altitude, vehicle position/location, etc. This information may be used to infer engine operating parameters, such as local barometric pressure, for example. Controller 12 may further be configured to receive information via the internet or other communication networks 13. In some examples, information received from the GPS may be cross-referenced to information available via the internet to determine local weather conditions, etc. Controller 12 may in some examples use the internet to obtain updated software modules which may be stored in non-transitory memory.

As described above, FIG. 1 shows only one cylinder of a multi-cylinder engine; however it should be appreciated that each cylinder may similarly include its own set of intake/exhaust valves, fuel injector, spark plug, etc.

In some examples the engine may be a diesel engine configured to combust diesel fuel (e.g. petroleum diesel or bio-diesel) via compression ignition. However, in other examples, the engine may not comprise a diesel engine. For brevity, FIG. 1 illustrates an engine where some of the components are included in a diesel engine, and where the rest of the components may be included in either a diesel engine or a non-diesel engine. As such, components specific to a diesel engine will be pointed out as being specific to a diesel engine, in the remaining description of FIG. 1.

Exhaust gas sensor 126 is shown coupled to exhaust passage 48 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. A detailed embodiment of a UEGO sensor is described with reference to FIG. 8. This sensor may be used for ambient humidity estimation under selected vehicle operating conditions. In some examples, the engine system may include dedicated ambient humidity sensors for measurement of ambient humidity when a humidity estimation is triggered. A change in ambient temperature as measured or estimated from OAT 127 and/or IAT sensor 125 may be used as a trigger for humidity measurement. Similarly, a change in ambient pressure as estimated by the BP sensor 128 may trigger a humidity measurement. If a difference between the current ambient temperature or pressure and the ambient temperature or pressure at the last known humidity measurement is higher than a threshold, a humidity measurement may be triggered. The humidity sensors may be positioned at the intake passage 42 and/or at the exhaust passage 48 upstream of an emission control device 70. By actively sensing humidity during ambient conditions when humidity is expected to change, rather than (or in addition to) opportunistically sensing humidity when possible, a more accurate and reliable humidity estimate may be provided for engine control and also unnecessary humidity measurements may be avoided.

In some examples, a humidity estimate may be conducted via either the ultrasonic sensors, or via another means, such as UEGO sensor 126. Such a method may include indicating relative humidity from differences between pairs of reflected signals from a single ultrasonic sensor coupled to a vehicle, each of the reflected signals having substantially equivalent transit time from an object back to the ultrasonic sensor; indicating relative humidity from one or more sensors coupled to the vehicle other than the ultrasonic sensor (e.g. UEGO sensor); and selecting which relative humidity indication method to use in response to environmental or vehicle operating conditions. As such, humidity estimations may be timely and accurately inferred, which may improve vehicle operating conditions where such operating conditions rely on accurate humidity estimations.

Emission control device 70 is shown arranged along exhaust passage 48 downstream of exhaust gas sensor 126. Device 70 may include one or more of at least a three-way catalyst, lean NOx trap, diesel oxidation catalyst (DOC), selective catalytic reduction (SCR) catalyst, oxidation catalyst, etc. An ammonia (or urea) delivery system may be coupled to the SCR catalyst or upstream of the SCR catalyst to deliver reductant to the SCR catalyst.

In an example where the engine comprises a diesel engine, at least one diesel particulate filter (DPF) 72 may be coupled downstream of the emission control device 70 in order to trap soot. The DPF may be manufactured from a variety of materials including cordierite, silicon carbide, and other high temperature oxide ceramics. As such, the DPF may have a finite capacity for holding soot. Therefore, the DPF may be periodically regenerated in order to reduce the soot deposits in the filter so that flow resistance due to soot accumulation does not reduce engine performance. Filter regeneration may be accomplished by heating the filter to a temperature that will burn soot particles at a faster rate than the deposition of new soot particles, for example, 400-600° C. In one example, the DPF may be a catalyzed particulate filter containing a washcoat of precious metal, such as platinum, to lower soot combustion temperature and also to oxidize hydrocarbons and carbon monoxide to carbon dioxide and water.

In an example where the engine may comprise a diesel engine, a hydrocarbon (HC) reductant delivery system 74 may be used to deliver HC from the fuel tank or from a storage vessel to the exhaust system to generate heat for heating the particulate filter 72 for regeneration purposes. Alternatively, or in addition, late fuel injection (e.g., during an exhaust stroke) may be used to raise exhaust temperature.

Temperature sensors 76 and 78 may be located upstream and downstream, respectively of DPF 72, in the example case where the vehicle engine comprises a diesel engine. The temperature sensors 76 and 78, or additional temperature sensors, may also be located within the DPF, or DPF temperature (or exhaust temperature) may be estimated based on operating conditions using an exhaust temperature model. A differential pressure signal may be determined from pressure sensors 80 and 82 upstream and downstream of DPF 72, respectively. Note that a single differential pressure may also be used to measure the differential pressure across DPF 72. A single port gauge pressure sensor (SPGS) may also be used.

It should be appreciated that alternate emission control system configurations may be used in alternate embodiments. For example, emission control device 70 may be coupled downstream of the DPF. Further in other examples, a plurality of diesel particulate filters may be included in the emission control system. Still further, in other examples the SCR catalyst may not be included in the emission control system. Each catalyst, filter, etc., may be enclosed within a single housing or alternatively may be enclosed via separate housings. It will be appreciated that numerous configurations are possible and the configuration depicted in FIG. 1 is exemplary in nature. Further still, as noted above, a reductant (e.g., ammonia or urea) injection system may be coupled to the exhaust to inject urea upstream of emission control device 70.

To regenerate the DPF a regeneration injection strategy may be implemented. The regeneration injection strategy may implement an injection profile including a plurality of injection events such as a pilot fuel injection, a main fuel injection, a near post fuel injection, and/or a far post fuel injection. It will be appreciated that the aforementioned fuel injections may include a plurality of injection events, in other embodiments. Thus, the DPF may be regenerated during operation of the engine. For example, the temperature downstream of a DOC and upstream of a DPF may be controlled to a desired value to promote combustion of particulate matter within the DPF, by adjustment of the amount of the various injections. In this example, a temperature set-point downstream of the DOC and upstream of the DPF may be established to facilitate regeneration of the DPF. In still further examples, a heater 75 configured to raise temperature of the DPF may be utilized for DPF regeneration.

As discussed, regeneration of the DPF coupled to an underbody of a motor vehicle may include burning of particulate (e.g. soot) stored in the particulate filter, which may result in hot gases exiting a rear (e.g. exhaust) of the motor vehicle. Thus, in some examples it may be desirable to indicate whether an object is indicated to be below a threshold distance away from the exhaust. Such an object may be identified via one or more onboard camera(s) (e.g. 186), and/or one or more ultrasonic sensor(s) (e.g. 185), for example. In some examples, selecting an ultrasonic sensor to use in conducting a distance measurement between the sensor and an object may include selecting the selected sensor based on a transmission path of the selected sensor overlapping at least a portion of the hot gases exiting the rear of the motor vehicle, and may further be based on the object being within a transmission path of the selected sensor as identified by one of the cameras. In such a case, if an object is indicated to be less than a threshold distance away from the exhaust (within a threshold distance of the hot gases exiting the rear of the motor vehicle), the DPF regeneration procedure may be postponed, or aborted, for example. Furthermore, ambient humidity and ambient temperature may affect the thermal conductivity of air, and thus in some examples it may be desirable to obtain measurements of ambient temperature and humidity, such that a threshold distance that the object may be away from the exhaust may be adjusted according to the thermal conductivity of air. More specifically, in some examples, thermal conductivity of air may be determined based on an indication of relative humidity and air temperature, where air temperature is measured near where the hot gases exit the rear of the motor vehicle, and wherein adjusting the threshold distance based on the measured thermal conductivity of air may include decreasing the distance threshold as thermal conductivity decreases, and increasing the distance threshold as thermal conductivity increases. In this way, DPF regeneration procedures may be commenced and completed more frequently than if the distance threshold were not adjustable. Furthermore, responsive to an indication that an object is positioned at a greater distance than the threshold distance, the object and an area proximate the rear of the vehicle may continue to be monitored during conducting the regeneration procedure via the one or more cameras and/or ultrasonic sensor(s). In such an example, if the object or other object is identified as being closer than the adjusted threshold distance during the regeneration procedure, the regeneration procedure may be terminated.

Turning to FIG. 2, an exemplary parking assist system 200 employing the use of an ultrasonic sensor 185 is schematically shown. The system 200 includes components of a typical vehicle including a powertrain control module 208 illustrated as a combined control unit consisting of the controller 12 and transmission control unit 210. The system 200 further includes one or more ultrasonic sensor(s) 185, mounted on the vehicle in various locations, and configured to provide inputs to a parking assistance module 205. For example, ultrasonic sensors may be placed on a front, a side, a rear, or any combination of the front, rear, and/or side of the vehicle. Such a system 200 described in this disclosure is generally applicable to various types of vehicles, including small or large cars, trucks, vans, SUV's, etc., that may employ an ultrasonic sensor.

The term "power train" refers to a power generating and delivery system that includes an engine and a transmission, and is used as a drive system in an automotive vehicle. The power train control module 208 performs engine and transmission control operations using a controller 12 and a transmission control unit 210, respectively. The controller 12 detects data from various portions of the engine and may adjust fuel supply, ignition timing, intake airflow rate, and various other known engine operations, as discussed above with regard to FIG. 1. The transmission control unit 210 detects engine load and vehicle speed to decide a gear position to be established in the transmission. For the purpose of description, FIG. 2 depicts only a few components of the power train control module 210. Those skilled in the art, however, will understand that the power train control module 208 may be operatively coupled to a number of sensors, switches, or other known devices to gather vehicle information and control various vehicle operations.

The parking assistance module 205 provides capabilities such as auto-parking, parallel parking, obstacle identification, and so on, resulting in a convenient or completely automatic parking process. For example, using the parking assistance module 205, the vehicle may steer itself into a parking space with little or no input from the driver. In that process the module detects and warns about objects that pose an impact risk. Detection and warning are performed by a number of sensors, such as the ultrasonic sensor 185, which cooperate to determine the distance between the vehicle and surrounding objects. However, as discussed above and which will be discussed in further detail below, humidity may be a noise factor contributing to operational use of the ultrasonic sensor. Accordingly, in some examples, relative humidity may be determined via either the ultrasonic sensor itself, or via other sensors (e.g. UEGO sensor) in the vehicle, such that operational use of the ultrasonic sensor may be improved. In some examples, one or more camera(s) positioned at one or more location on the vehicle may be utilized to detect objects of interest, such that a humidity calculation may be conducted via the ultrasonic sensor(s), described in further detail below. In such an example, a method may include selecting one of a plurality of ultrasonic sensors positioned around a motor vehicle based in part on one or more images from one or more cameras positioned around the motor vehicle. The selected sensor may in some examples be selected based on an object, identified by one of the cameras, being within a transmission path of the selected sensor. The object may in some examples be indicated to be stationary with respect to the vehicle. For example, it may be indicated via the cameras that the object is stationary, in some examples. In another example, the selected sensor may be selected based on there being a target vehicle traveling within a transmission path of the selected sensor and where the target vehicle is traveling at a velocity substantially equal to the motor vehicle velocity and also at a substantially constant distance from the motor vehicle. Furthermore, in some examples, the one or more camera(s) may function to additionally or alternatively communicate images and rough distance indications (e.g. via object recognition analysis) during an assisted or fully automated parking procedure.

The ultrasonic sensor 185 may detect obstacles on either side, in the front, or the rear of the vehicle, and vehicle modules, such as a steering wheel module (not shown), brake system (not shown), parking assistance module (205), etc., may utilize such information. Thus, while the one or more ultrasonic sensor(s) 185 are illustrated coupled to the parking assistance module, such a depiction is for illustrative purposes only, and is not meant to be limiting. For the sake of brevity, however, in-depth description of other potential uses of one or more ultrasonic sensor(s) will not be discussed herein. However, it may be understood that uses of the ultrasonic sensor(s) other than parking assistance may be utilized according to the methods described herein, without departing from the scope of the present disclosure.

The one or more ultrasonic sensor(s) 185 may be configured to include a transmitting (sending) means, adapted to transmit ultrasonic waves, and a receiving means, adapted to receive the waves reflected from an object in the vicinity of the vehicle, such as obstacle 220. A transit time comprising a time between transmitting and receiving the ultrasonic wave signal may be determined, and a distance between the sensor and the obstacle (for example) may be indicated based on the formula $d=t*c/2$, where c is the speed of sound and t is the transit time. This distance information may then be provided to the parking assistance module 205 (or other relevant module), for example. Such object detection capabilities of ultrasonic sensors are well known to those skilled in the art and will not be discussed in detail in the present disclosure.

As discussed above, operational use of the one or more ultrasonic sensors 185 may be subject to noise factors. The four main noise factors that affect ultrasonic sensors are temperature, humidity, target surface angle, and reflective surface roughness. However, as will be discussed in further detail below, temperature may be compensated for by measuring air temperature. Furthermore, target surface angle and reflective surface roughness may be compensated for by the use of two or more wave frequencies sent from a single transmitting means, where only reflected signals which have the same transit time from transmission to receipt are utilized to determine distance measurements, discussed in further detail below. However, for vehicles without a dedicated humidity sensor, compensating for humidity may be challenging.

Thus, methods for determining, and compensating, for humidity via the use of an ultrasonic sensor (e.g. 185), are described in further detail below with regard to FIGS. 4-7, FIG. 9, and FIGS. 11-12. Briefly, humidity differentially affects an amount of attenuation (e.g. loss in intensity) observed for different frequencies of sound. Thus, by transmitting a plurality of ultrasonic frequencies from an ultrasonic sensor and determining attenuation of each of the individual frequencies, relative humidity may be calculated as a function of the difference in attenuation between the pairs of frequencies. However, in some examples, certain frequencies may be better suited for determining differences in attenuation between pairs of frequencies. Accordingly, some examples may include changing frequencies of the transmitted signals responsive to a determination that the reflected signals have, or would have, undesired signal-to-noise ratio(s).

For example, certain environmental conditions (e.g. wind, rain, snow, fog, temperature fluctuations, etc.), may affect a signal-to-noise ratio of particular frequencies. As such, if a particular frequency is indicated to have undesirable signal-to-noise, in other words, attenuation is too great, then one or more additional frequency(s) may be transmitted and received such that only frequency(s) with desired signal-to-noise ratios may be utilized for conducting a relative humidity measurement.

Thus, changing the frequency(s) of the transmitted signals may include changing the frequency(s) responsive to environmental conditions including one or more of the following: ambient temperature, ambient humidity, and a transit time from transmission to receipt of the transmitted and reflected signals.

For example, a previous humidity estimation may in some examples be used as a reference for changing frequency(s) to achieve desired signal-to-noise ratios. As an example, if humidity is indicated to likely be high based on a previous humidity estimation, where the previous humidity estimation may be stored at the controller, then one or more frequency(s) may be excluded and another frequency selected, where the selected frequency may be a frequency likely to exhibit a desired signal-to-noise ratio of the transmitted and received signal.

Similarly, in some examples, changing frequency(s) may be a function of an indicated ambient temperature. In still further examples, changing frequency(s) may be a function of indicated transit time from transmission to receipt of the transmitted and reflected signals. For example, if a transit time from transmission to receipt of the transmitted and reflected signals is not within an expected range, then it may be indicated that an environmental or other condition is affecting signal-to-noise and/or integrity of the transmitted and received signal, and the frequency may be changed in an attempt to increase the signal-to-noise ratio and/or the integrity of the signal. In one example, such a condition affecting transit time from transmission to receipt of the transmitted and reflected signals may include a dirty ultrasonic sensor. Such an example may include comparing amplitude of the reflected signal to a reference amplitude based on a distance of an object from which the selected signal is reflected, and environmental conditions including, but not limited to, humidity or temperature to determine whenever the sensor needs to be cleaned. In an example where the sensor may need to be cleaned, changing frequency(s) may alleviate the issue. In still other examples, a different ultrasonic sensor (instead of the dirty ultrasonic sensor) may be selected, where the different ultrasonic sensor may be selected responsive to an indication that the transmission path of the ultrasonic sensor overlaps with an object of interest to be utilized for conducting a relative humidity estimate. Said another way, in some examples selecting one of a plurality of sensors positioned around the motor vehicle may be based in part on whether any of the plurality of sensors need to be cleaned.

Turning now to FIG. 3A, a graph 300 depicting sound attenuation as a function of percent relative humidity, is shown. More specifically, percent relative humidity is illustrated on the x-axis, and sound attenuation in dB/km is illustrated on the y-axis. Line 302 indicates ultrasonic frequency at 100 kHz, line 304 indicates 80 kHz, line 306 indicates 63 kHz, line 308 indicates 50 kHz, line 310 indicates 40 kHz, line 312 indicates 31.5 kHz, line 314 indicates 25 kHz, and line 316 indicates 20 kHz. As illustrated, sound attenuation increases as ultrasonic wave frequency increases.

Figure 3B:
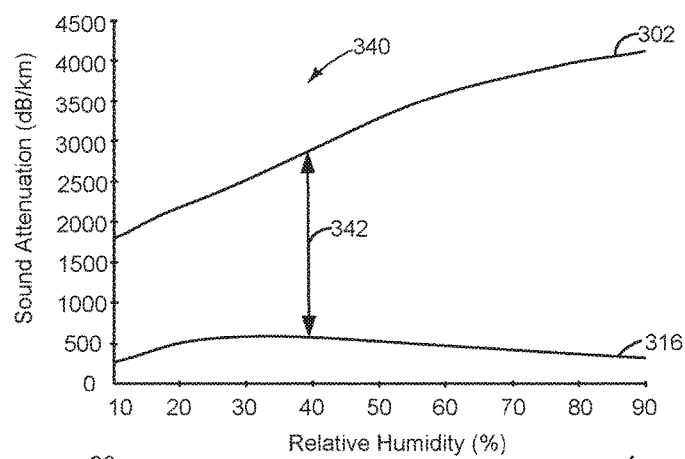
FIG. 3B depicts a graph illustrating a difference in sound attenuation for different ultrasonic frequencies, at a particular relative humidity.

Turning now to FIG. 3B, a graph 340 depicting sound attenuation as a function of percent relative humidity is again illustrated. As in FIG. 3A, line 302 indicates ultrasonic frequency at 100 kHz, and line 316 illustrates ultrasonic frequency at 20 kHz. For illustrative purposes, arrow 342 is depicted, indicating the difference in attenuation at forty percent relative humidity between ultrasonic frequency at 100 kHz and 20 kHz.

Figure 3C:
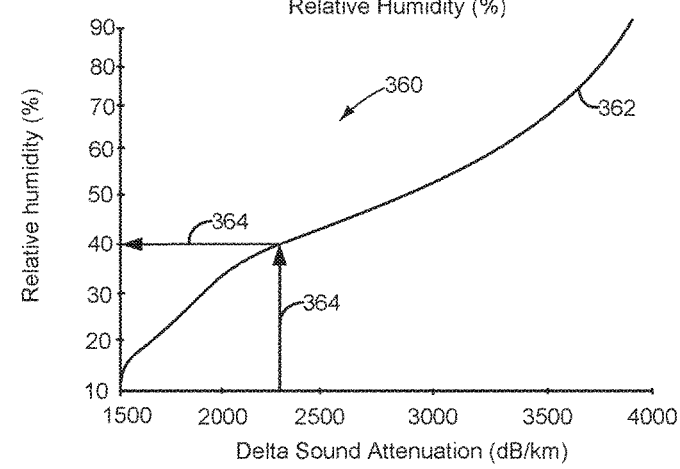
FIG. 3C graphically depicts an example transfer function for determining relative humidity as a function of a difference in sound attenuation for two ultrasonic frequencies.

Accordingly, turning to FIG. 3C, graph 360 is shown depicting a difference in sound attenuation 362 between 100 kHz and 20 kHz, across the range of percent relative humidity indicated in FIGS. 3A-3B. More specifically, the difference in sound attenuation (delta sound attenuation) between 100 kHz and 20 kHz is illustrated on the x-axis, and percent relative humidity is indicated on the y-axis. By plotting differences in attenuation between two frequencies as a function of percent relative humidity, a simple transfer function, represented by arrows 364 may be used to determine relative humidity. Said another way, conversion of the difference in attenuation may comprise the use of a transfer function to convert the difference in attenuation into a measurement of relative humidity. For example, a two dimensional (2D) lookup table may include known, or predetermined, values corresponding to relative humidity as a function of differences in sound attenuation between different frequencies. Once the difference in sound attenuation between two different frequencies is known, such a lookup table may be used to indicate relative humidity. While differences in sound attenuation are illustrated for 100 kHz and 20 kHz, it may be understood that the use of such frequencies to determine relative humidity are for illustrative purposes only, and differences in sound attenuation between two frequencies corresponding to frequencies other than 100 kHz and 20 kHz may be similarly utilized.

Turning to FIG. 4, a high level flowchart for an example method 400 for determining humidity via the use of an ultrasonic sensor, is shown. More specifically, method 400 may include transmitting a plurality of signals from a single sensor, each at a different frequency, receiving reflected signals of the transmitted signals, and determining attenuation values only for each of the reflected signals which have the same transit time from transmission to receipt. Responsive to determining attenuation values, method 400 may further include determining differences between pairs of the attenuation values, and converting the differences to an indication of relative humidity.

Method 400 will be described with reference to the systems described herein and shown in FIG. 1 and FIG. 2, though it should be understood that similar methods may be applied to other systems without departing from the scope of this disclosure. Method 400 may be carried out by a controller, such as controller 12 in FIG. 1, and may be stored at the controller as executable instructions in non-transitory memory. Instructions for carrying out method 400 and the rest of the methods included herein may be executed by the controller based on instructions stored on a memory of the controller and in conjunction with signals received from sensors of the engine system, such as the sensors described above with reference to FIG. 1. The controller may employ actuators, such as ultrasonic sensor (e.g. 185), etc., according to the method below.

Method 400 begins at 405 and may include determining engine operating parameters. Operating conditions may be estimated, measured, and/or inferred, and may include one or more vehicle conditions, such as vehicle speed, vehicle location, etc., various engine conditions, such as engine status, engine load, engine speed, A/F ratio, etc., various fuel system conditions, such as fuel level, fuel type, fuel temperature, etc., various evaporative emissions system conditions, such as fuel vapor canister load, fuel tank pressure, etc.

Continuing to 410, method 400 may include measuring ambient air temperature. As discussed above with regard to FIG. 1, an outside air temperature (OAT) sensor (e.g. 127) positioned on the exterior of the vehicle system (e.g. 101) may be used to determine ambient air temperature. For example, controller (e.g. 12) may send a signal to OAT sensor to take a reading of ambient air temperature. The reading may then be communicated back to the controller, and may be stored at the controller, for example. As will be discussed in further detail below, knowledge of ambient air temperature may be taken into account when calculating total attenuation difference between two given ultrasonic frequencies. Said another way, converting distances between pairs of attenuation values to an indication of relative humidity may rely on measured ambient air temperature.

Proceeding to 415, method 400 may include performing a Variable Frequency Algorithm (VFA), consisting of sending and receiving a plurality of ultrasonic frequencies, such that difference(s) in attenuation may be calculated. Performing the (VFA) may be conducted according to method 500, depicted in FIG. 5.

Accordingly, turning to FIG. 5, a high level flowchart for an example method 500 for conducting the VFA, is shown. More specifically, method 500 may include commanding the ultrasonic sensor to transmit an ultrasonic wave (chirp signal) at a first frequency, and then measuring and storing a transit time and intensity of the resulting echo. Next, method 500 may include commanding the ultrasonic sensor to transmit another chirp at a second frequency, and may further include subsequently measuring and storing transit time and intensity of the resulting echo corresponding to the second chirp signal.

Method 500 will be described with reference to the systems described herein and shown in FIG. 1 and FIG. 2, though it should be understood that similar methods may be applied to other systems without departing from the scope of this disclosure. Method 500 may comprise a sub-method of method 400, and thus method 500 may be carried out by the controller (e.g. 12), and may be stored at the controller as executable instructions in non-transitory memory. Instructions for carrying out method 500 and the rest of the methods included herein may be executed by the controller based on instructions stored on a memory of the controller and in conjunction with signals received from sensors of the engine system, such as the sensors described above with reference to FIG. 1. The controller may employ actuators, such as ultrasonic sensor (e.g. 185), etc., according to the method below.

Method 500 begins at 505 and may include transmitting a chirp signal at a first frequency. More specifically, the controller may command an electronic signal in the form of an oscillated voltage to the ultrasonic sensor (e.g. 185), where the frequency of the oscillated voltage may correspond to the desired frequency of the resultant ultrasonic wave. In some examples, the first frequency may comprise a frequency for which a greatest amount of attenuation would be expected, for example 100 kHz. However, such an example is illustrative and not meant to be limiting. Instead, any frequency between and including 20 kHz-100 kHz may be first transmitted.

Continuing to 510, method 500 may include measuring and storing the transit time (t1) and intensity (i1) of the resulting echo corresponding to the transmitted chirp at the first frequency (f1). For example, the ultrasonic sensor may be configured to convert the received echo (received sound wave) into an oscillating voltage, where an electric potential of the oscillating voltage may correspond to the intensity of the ultrasonic wave. A decrease in intensity of the resulting echo may be understood to be indicative of the attenuation of the ultrasonic wave from transmission to receipt.

Upon receiving the echo corresponding to the transmitted chirp signal at the first frequency, method 500 may proceed to 515. At 515, method 500 may include transmitting a chirp signal at a second frequency (f2). Importantly, it may be understood that the resultant echo of the first frequency may be first received by the ultrasonic sensor, prior to sending out the second chirp signal. The second chirp signal may be different in frequency than the first chirp signal, and may correspond to a frequency greater than, or less than the first chirp signal frequency. For example, if the first frequency (f1) was 100 kHz, then the second frequency (f2) may be 20 kHz. Such an example is illustrative and is not meant to be limiting.

Proceeding to 520, similar to step 510, method 500 may include measuring and storing transit time (t2) and intensity (i2) of the resulting echo corresponding to the second chirp signal. As discussed above, transit time and intensity of the second chirp signal may be stored at the controller (e.g. 12).

Proceeding to 525, method 500 may include determining whether additional accuracy (e.g. better signal-to-noise) may be desired. For example, responsive to the sending and receiving of the first two ultrasonic waves (chirp signals), the controller may determine whether signal-to-noise of the received ultrasonic waves are sufficient (above a predetermined threshold level) for analysis. In some examples, depending on a contour and/or reflective angle of an object that is reflecting the transmitted waves, one or more of the received signals may be below a threshold desired for accurate measurement of attenuation. In another example, environmental conditions (e.g. wind, rain, etc.) may result in one or more of the received signals being below the predetermined threshold level. In another example, environmental conditions may include one or more of the following: ambient temperature, ambient humidity, and the transit time from transmission to receipt of the transmitted and the reflected signals. In still further examples, a dirty ultrasonic sensor may result in one or more of the received signals being below the predetermined threshold level.

In still other examples, additional accuracy may be desired based on the intended use of a humidity measurement via the ultrasonic sensor. As an example, if a humidity estimation were previously indicated via another means (e.g. UEGO, etc.), and the ultrasonic sensor is being used as a check to verify that the prior measurement is, in fact, still correct, a precisely accurate measurement may not be desired. In such an example, if the signal-to-noise of the echoes received from the transmitted first and second frequencies is above the predetermined threshold, then only two frequencies may be utilized for determining an estimation of humidity. However, there may be other examples where more precise measurements of relative humidity may be desired. Such an example may include a condition where a duration of time has elapsed since a previous humidity measurement, where a change in barometric pressure is indicated to have changed greater than a threshold amount, where a change in temperature is indicated to have changed greater than a threshold amount, wherein accurate humidity inference is desired for engine operation, or for parking assistance, etc.

In any of the above-mentioned examples, or other examples not specifically mentioned, where additional accuracy is desired, method 500 may proceed to 530. At 530, method 500 may include commanding the ultrasonic sensor to transmit one or more additional chirp signals (e.g. change frequencies), each of which may be measured as described above for transit time and return echo intensity, by the ultrasonic sensor. As an example, a third, fourth, and fifth frequency may be transmitted and each monitored for transit time and return echo intensity. Such an example is meant to be illustrative, and not meant to be limiting. However, it may be understood that accuracy of the resulting humidity measurement, which will be described in detail below, may be increased with increasing numbers of frequencies transmitted and received. Said another way, frequencies of the transmitted signals may be changed responsive to a determination that the reflected signals have or would have a desired signal-to-noise below a predetermined threshold level, and wherein changing frequencies of the transmitted signals occurs prior to determining differences between pairs of the attenuation values and converting differences to an indication of relative humidity, as will be discussed in further detail below.

Returning to 525, responsive to the two or more received frequencies being of sufficient signal-to-noise for the desired accuracy of the resulting humidity measurement (described below), method 500 may return to step 420 of FIG. 4.

At step 420 of FIG. 4, method 400 may include indicating whether transit times for each of the frequencies are equivalent. For example, if two frequencies were transmitted and received at step 415, then it may be determined whether the two frequencies both have the same transit time. If three frequencies were transmitted and received at step 415, then it may be determined whether all three of the frequencies have the same transit time, etc. In calculating differences in attenuation in order to determine relative humidity, only those frequencies that have the same transit times may be further processed, as will be discussed in further detail below. More specifically, attenuation values may be determined only for each of the reflected signals which have the same transit time from transmission to receipt, which may correct for variations in target surface angle and reflective surface roughness, for example.

Accordingly, if it is indicated at step 420 that all of the transit times for each of the frequencies transmitted and received at step 415 are equivalent, method 400 may proceed to 425.

At 425, method 400 may include performing a Delta Attenuation Calculation (DAC) according to the method depicted in FIG. 6.

Turning now to FIG. 6, a high level example method 600 for performing a DAC, is shown. More specifically, frequencies that were transmitted and received according to the variable frequency algorithm (VFA) described above with regard to FIG. 5, and which were indicated to have the same transit times described above with regard to FIG. 4, may be processed in order to calculate attenuation of each of the individual frequencies, which may then be used to calculate differences in attenuation between frequencies such that relative humidity may be determined.

Method 600 will be described with reference to the systems described herein and shown in FIG. 1 and FIG. 2, though it should be understood that similar methods may be applied to other systems without departing from the scope of this disclosure. Method 600 may comprise a sub-method of method 400, and thus method 600 may be carried out by the controller (e.g. 12), and may be stored at the controller as executable instructions in non-transitory memory. Instructions for carrying out method 600 and the rest of the methods included herein may be executed by the controller based on instructions stored on a memory of the controller and in conjunction with signals received from sensors of the engine system, such as the sensors described above with reference to FIG. 1.

Method 600 begins at 605 and may include calculating attenuation ($\alpha$) for each frequency with equivalent transit times as indicated by method 400 of FIG. 4. More specifically, calculating attenuation for a first frequency (f1) may be conducted based on the following formula $$S1 = S0 * e^{\wedge}(-\alpha 1 * z); \quad (1)$$

where S0 is the original intensity of the non-attenuated signal, z is the distance the signal travels, S1 is the intensity of the received attenuated signal, and $\alpha 1$ is the attenuation coefficient for frequency f1.

Rearranging equation (1), gives $$\text{Attenuation} = \alpha 1 = \ln(S1/S0)/-z. \quad (2)$$

A total attenuation coefficient ($\alpha$Tot) is comprised of attenuation due to temperature, humidity, target surface angle, and reflective surface roughness. However, by conducting the VFA according to the method depicted in FIG. 5, and by further ensuring that only those frequencies with the same transit times are processed for the DAC, as illustrated by the method depicted in FIG. 4, the effects of temperature, target surface angle, and reflective surface roughness may be subtracted out. More specifically, because temperature is known its effect may be cancelled out, and target surface angle and reflective surface roughness does not change during differential measurement of frequency echo intensity, provided that transit times for each of the frequencies analyzed are equivalent. Thus, of the variables that affect the total attenuation coefficient ($\alpha$Tot), only humidity is not known and may have a different attenuation coefficient for different frequencies.

Accordingly, after all attenuation values have been calculated for each of the analyzed frequencies at 605, method 600 may proceed to 610. At 610, method 600 may include calculating the delta ($\Delta$) attenuation values for each of the analyzed frequencies. More specifically, delta attenuation due to humidity between two frequencies, f1 and f2 for example, may be equal to total delta attenuation between f1 and f2, for the reasons described above. Thus $$\Delta\alpha\text{Humidity}(f1\text{-}f2) = \Delta\alpha\text{Total}(f1\text{-}f2) = \Delta\alpha(f1\text{-}f2). \quad (3)$$

As illustrated by equation 3, two frequencies f1 and f2 are shown. However, it may be understood that in an example where more than two frequencies may be utilized in order to perform the VFA depicted in FIG. 5, and the DAC depicted herein with regard to FIG. 6, each frequency utilized may be subtracted from all other frequencies in order to increase accuracy of the delta attenuation measurement. Taking three frequencies as an example, where the three frequencies comprise f1, f2, and f3, the delta attenuation calculation may comprise (f1-f2), (f1-f3), and (f2-f3), where the differences may comprise absolute values of the respective differences. Similar methodology may apply to examples where more than three frequencies may be utilized.

Proceeding to 615, once $\Delta$attenuation has been calculated for each pair of frequencies, method 600 may include storing the $\Delta$attenuation values and corresponding frequency values into a table, where the table may be stored at the controller (e.g. 12). Method 600 may then return to step 425 of method 400.

Accordingly, returning to step 425 of method 400, once the DAC has been conducted according to method 600 depicted in FIG. 6, method 400 may proceed to 430. At 430, method 400 may include determining relative humidity using a lookup table stored at the controller. For example, a simple transfer function may be utilized such that, for a given pair of frequencies and a given $\Delta$attenuation for the given pair of frequencies, relative humidity may be determined by correlating the transfer function with the lookup table stored at the controller (see FIG. 3C). In a case where multiple $\Delta$attenuation values for multiple pairs of frequencies are obtained, each $\Delta$attenuation value and corresponding pair of frequencies may be used to obtain a percent relative humidity, and all the relative humidity values may then be averaged by the controller in order to increase confidence in the relative humidity measurement.

Returning to 420 of method 400, if it is indicated that not all of the transit times for the frequencies utilized at step 415 are indicated to be equivalent, method 400 may proceed to 435 and may include selectively discarding non-equivalent data. For example, data corresponding to frequencies that have the same transit times may be stored at the controller (e.g. 12), while data from frequencies without other equivalent transit times may be discarded. Proceeding to 440, it may be indicated whether the remaining data set is sufficient for determining humidity with the desired accuracy. As an example, if only two frequencies were indicated to have the same transit times, but increased accuracy is desired, where the increased accuracy may comprise calculating relative humidity from a data set comprising more than two frequencies, then method 400 may proceed to 445. Thus, at 440, if it is indicated that the remaining data set is not sufficient for calculating relative humidity with the desired accuracy, method 400 may proceed to 445 and may include determining humidity in another way, where conditions allow. In some examples, determining humidity may be accomplished via the use of intake or exhaust gas oxygen sensor(s), as will be discussed with regard to FIGS. 8-9. Alternatively, if at 440, it is indicated that the remaining data set is sufficient for determining relative humidity with the desired accuracy, method 400 may proceed to 425, and may include performing the DAC as described above.

In some examples, a vehicle may be equipped with a plurality of ultrasonic sensors. In such a case, there may be instances where it may be beneficial to prioritize the use of a particular sensor when conducting a relative humidity measurement. Such examples may include a condition where one or more sensors are indicated to be dirty, or not functioning as desired. In such a case, it may be beneficial to only use the ultrasonic sensor(s) that are functioning as desired. In another example, it may be beneficial to detect an object by a secondary means, and then preferentially use an ultrasonic sensor positioned in an optimal location in order to increase the likelihood of a successful relative humidity determination. In some examples, detecting an object by a secondary means may comprise detecting an object via the use of one or more onboard camera(s) (e.g. 186).

For example, one or more camera(s) may be physically wired and communicatively coupled to a control system of the vehicle including a controller (e.g. 12). In another example, one or more camera(s) may be additionally or alternatively in wireless communication with the controller, for sending and receiving data transmissions. Wired communication may comprise USB technology, IEEE 1394 technology, optical technology, other serial or parallel port technology, or any other suitable wired link. Additionally or alternatively, wireless communication with the one or more camera(s) may comprise Bluetooth, an IEEE 802.11 protocol, an IEEE 802.16 protocol, a cellular signal, a shared Wireless Access Protocol-Cord Access (SWAP-CA) protocol, a wireless USB protocol, or any other suitable wireless technology. The controller may receive one or more data files from the one or more cameras, such as video data files, image data files, etc.

The one or more cameras may include cameras mounted on the front or rear bumper, or any other suitable location on the front or rear of the vehicle. In some examples, more than one camera may be mounted on the front and/or rear. For example, two or more cameras may be mounted on the front of the vehicle, and two or more cameras may be mounted on the rear of the vehicle. Similarly, one or more side-facing cameras may be positioned at any suitable location on the vehicle in order to image objects on either or both of a left side of the vehicle, and a right side of the vehicle. In some examples, more than one camera may be utilized to capture images corresponding to the left side of the vehicle, and more than one camera may be utilized to capture images corresponding to the right side of the vehicle.

In some examples, the one or more cameras may be fixed, while in other examples the one or more cameras may be moveable or rotatable relative to the vehicle. Further, some examples may include one or more fixed cameras, and one or more moveable cameras. Position of the one or more cameras on the vehicle may in some examples enable 360° viewing capabilities. As discussed, the one or more cameras may include cameras for capturing videos and/or images. In other examples, the one or more cameras may comprise infrared cameras. Some implementations may include a plurality of cameras, some of which may be configured for capturing image and/or video, while one or more other cameras may be configured to capture infrared images.

In some examples, the one or more cameras may be configured to detect objects in the vicinity of the vehicle. For example, object detection systems (often referred to as obstacle detection systems) that operate via the use of one or more vehicle cameras, are well known in the art. More specifically, vehicle safety systems are widely known that enable detection of obstacles such as pedestrians, bicycles, road blocks, other cars, etc. An in depth discussion of all possible variations of object recognition via the use of one or more camera(s) is outside the scope of the present disclosure. However, it may be understood that any method known by those skilled in the art may be utilized to conduct object recognition via the use of one or more camera(s), as will be discussed in further detail below. As an illustrative example, one method of object recognition may include edge detection techniques, such as the Canny edge detection, to find edges in an image frame acquired by the one or more cameras. An edge-image corresponding to the image frame may then be generated. Furthermore, a binary image corresponding to the edge-image may also be generated. Subsequently, one or more "blobs" in the binary image corresponding to one or more objects, or obstacles, may be identified. Based on an analysis of the blobs in the binary image, information such as shape, relative size, relative distance, etc., of each of the blobs corresponding to objects may be determined. As discussed, such an example is meant to be illustrative, and in no way limiting. Other methods and systems for object detection via the use of one or more cameras that are known in the art may be readily utilized without departing from the scope of the present disclosure.

In some examples, object detection via the one or more cameras may be carried out while the vehicle is stationary. In other examples, object detection via the one or more cameras may be carried out while the vehicle is in motion. In either example, identified objects may be indicated to be stationary with respect to the vehicle if the identified object does not change in position, size, or shape, over a particular time period. For example, multiple images may be captured from the one or more cameras over a predetermined time period, and if position, size, and shape of a particular identified object does not change over the predetermined time period, it may be indicated that the identified object is stationary with respect to the vehicle. In one example, such an object that may be stationary with respect to the vehicle may be another vehicle traveling either in front of, on a left or right side of, or in back of, where both vehicles are traveling at substantially the same velocity and direction. As will be discussed below, identification of stationary objects with respect to the vehicle may be utilized in order to select from a plurality of ultrasonic sensors positioned on the vehicle, in order to conduct relative humidity measurements with increased likelihood of attaining accurate measurements.

Turning now to FIG. 7, a high level example method for detecting objects with one or more available cameras positioned on a vehicle, such that an ultrasonic sensor may be selected to conduct a relative humidity measurement, is shown. More specifically, one or more cameras may be configured to search an environment surrounding (e.g. proximal) the vehicle for objects that are stationary with respect to the vehicle. Responsive to identification of a suitable object, an ultrasonic sensor may be selected from a plurality of ultrasonic sensors positioned on the vehicle, to conduct a relative humidity measurement. In this way, a relative humidity measurement may be conducted with an increased likelihood of an accurate measurement of relative humidity being attained, and without unnecessary use of ultrasonic sensors under conditions where an accurate relative humidity measurement is not likely. By obtaining accurate relative humidity measurements, certain vehicle operating procedures, such as assisted or fully automated parking features, an amount of exhaust gas recirculation, an amount of spark retard, etc., may be more effectively controlled.

Method 700 will be described with reference to the systems described herein and shown in FIG. 1 and FIG. 2, though it should be understood that similar methods may be applied to other systems without departing from the scope of this disclosure. Method 700 may be carried out by a controller (e.g. 12), and may be stored at the controller as executable instructions in non-transitory memory. Instructions for carrying out method 700 and the rest of the methods included herein may be executed by the controller based on instructions stored on a memory of the controller and in conjunction with signals received from sensors of the engine system, such as the sensors described above with reference to FIG. 1. The controller may employ actuators, such as ultrasonic sensor (e.g. 185), one or more onboard camera(s) (e.g. 186), etc., according to the method below.

Method 700 begins at 705 and may include searching an environment around the vehicle with available cameras on the vehicle, in order to detect objects suitable for conducting a relative humidity measurement. In some examples, searching the environment with available cameras may commence responsive to one or more conditions triggering a desired humidity measurement. For example, conditions triggering a humidity measurement may include an indicated change in ambient temperature greater than an ambient temperature threshold since a previous (e.g. last) humidity measurement. Another example may include a change in ambient pressure greater than an ambient pressure threshold since a previous (e.g. last) humidity measurement. Still other examples may include an indication of a change in weather conditions, indicated by activation of windshield wipers (not shown), as an example. More specifically, responsive to activation of the vehicle windshield wipers, a signal may be sent to the controller requesting a relative humidity measurement, which may include the controller first commanding the one or more cameras to scan the environment for suitable objects.

In still other examples, searching the environment with available cameras may commence responsive to a threshold time of engine operation elapsing, or responsive to a distance of vehicle travel being greater than a predetermined distance since a previous (e.g. last) humidity measurement.

As discussed above, in some examples the vehicle may be equipped with an onboard navigation system (GPS) (e.g. 34) that includes one or more location sensors for assisting in estimating vehicle speed, vehicle altitude, vehicle position/location, etc. Such information may be used to infer local barometric pressure, for example, where a change in local barometric pressure greater than a threshold since a previous humidity measurement may trigger a request for a new humidity measurement, where suitable objects may be determined via onboard camera(s). In still further examples, the controller (e.g. 12) may be configured to receive information via the internet or other communication networks. Information received from the GPS may, in some examples, be cross-referenced to information available via the internet to determine local weather conditions, etc. In some examples, a change in weather conditions as indicated by GPS and cross-referenced to the internet may trigger a request for a relative humidity measurement, where available camera(s) may be utilized to scan the environment for suitable objects for conducting the relative humidity measurement.

In still further examples, there may be conditions of vehicle operation where the one or more available camera(s) are in operation (e.g. assist or fully-automated parking maneuvers), and where a relative humidity determination may be opportunistically conducted. As an example, if a vehicle is conducting a parking maneuver, where the parking maneuver involves the use of one or more onboard camera(s), if the camera(s) detect a suitable object for conducting a relative humidity measurement, a relative humidity measurement may be conducted, described in further detail below.

Accordingly, if conditions are met for searching the environment in proximity to the vehicle for suitable objects for conducting a relative humidity measurement, then at 705 of method 700, the one or more cameras may be activated in order to search for suitable objects. Specifically, a command may be sent from the controller (e.g. either a wired or wireless signal) to the one or more camera(s) to acquire one or more images of the environment around the vehicle. Images acquired by the one or more camera(s) may be stored at the controller, for example, for further processing, described in detail below. In some examples where one or more camera(s) are rotatable (e.g. movable, not fixed), the controller may be configured to capture images at different camera angles, such that the environment surrounding the vehicle may be accurately surveyed for suitable objects.

Discussed herein, suitable objects for conducting a relative humidity measurement may include but are not limited to objects above a predetermined threshold size, objects with a predetermined shape, objects that are indicated to be stationary with respect to the vehicle, objects with an indicated lack of surface roughness (e.g. smooth surface), objects with a preferred angle of orientation, etc. Suitable objects may further include objects that are likely to reflect an ultrasonic signal back to an ultrasonic sensor, such that the transit time from transmission to receipt of the signal may be the same for a plurality of individual ultrasonic frequencies.

Accordingly, responsive to a request to search the environment for suitable objects for conducting a relative humidity measurement, and responsive to acquiring images via the one or more camera(s) at step 705, method 700 may proceed to 710.

At 710, method 700 may include indicating whether suitable objects are detected by the one or more camera(s). As discussed above, object recognition analysis may be conducted by the controller using any means known in the art on images acquired from the one or more camera(s), in order to determine whether objects suitable for a relative humidity measurement are detected. In some examples, if multiple cameras are utilized in order to search the environment for suitable objects, the controller may process images from all of the cameras, and may further identify a best or most suitable object for conducting a relative humidity measurement. For example, in an example case where two cameras are utilized to search the environment, and where a suitable object is detected from both cameras, it may be further determined what object is most suitable for conducting a relative humidity test. One object being more suitable than another may include, but is not limited to, an object being larger in size than another object, an object having less surface roughness than another object, an object more stationary than another object with respect to the vehicle, etc.

Accordingly, if at 710, one or more suitable objects for conducting a relative humidity estimation are detected by the one or more camera(s), then method 700 may proceed to 715. At 715, method 700 may include indicating the suitable objects' position with respect to the vehicle. For example, indicating the suitable objects' position with respect to the vehicle may comprise indicating a position that the camera was facing at the time of image acquisition of the suitable object, and determining the location of the object as a function of direction the camera was facing. In some examples, one or more camera sensors (e.g. 187) may be used to send signals to the controller, indicating position of the one or more cameras. The controller may be configured to process the information on camera position, and based on an indication of camera position, a position of an identified suitable object relative to the vehicle may be indicated.

Proceeding to 720, method 700 may include indicating whether a vehicle is equipped with an ultrasonic sensor positioned to detect the identified suitable object for conducting a relative humidity measurement. For example, if the vehicle is equipped with a plurality of ultrasonic sensors, then a position and location of one or more of the ultrasonic sensors may be not be optimal for determining relative humidity based on the position of the identified suitable object. Accordingly, those ultrasonic sensors that are not optimally positioned may be excluded from conducting a relative humidity measurement. In other words, at 720, it may be determined which of a plurality of vehicle ultrasonic sensors is optimally positioned to conduct a relative humidity measurement based on the position of the identified suitable object. If, at 720, none of the available ultrasonic sensors are optimally positioned to conduct a relative humidity measurement based on the position of the identified suitable object with respect to the vehicle, then method 700 may return to 705, and may include continuing to search the environment surrounding the vehicle for suitable objects. In such an example, the identified suitable object for which an ultrasonic sensor was not available may be excluded from further analysis, such that only other suitable objects may be indicated in order to identify a suitable object for which an ultrasonic sensor is optimally positioned to conduct a relative humidity measurement.

In some examples, at 720, it may further be indicated as to whether the identified optimal ultrasonic sensor is functioning as desired. For example, if an ultrasonic sensor is identified as being optimal for detecting a particular identified suitable object, but that ultrasonic sensor is not functioning as desired, then method 720 may similarly return to step 705, and may include continuing to search for suitable objects with available cameras on the vehicle. In some examples, a particular ultrasonic sensor may be indicated to not be functioning as desired if it is dirty. A dirty ultrasonic sensor may be indicated, for example, based on amplitude and distance of a reflected signal. For instance, a transmitted signal that travels less than an expected distance prior to being reflected back to be received by the sensor may be indicative of a dirty ultrasonic sensor. Other examples of an ultrasonic sensor that is not functioning as desired may include any indication that function of the ultrasonic sensor is compromised. Illustrative examples may include an ultrasonic sensor with faulty wiring, degraded components, etc.

Accordingly, if, at 720, the optimal ultrasonic sensor for detecting a particular suitable object is indicated to not be functioning as desired, then the cameras may be further utilized in order to identify a suitable object for conducting a relative humidity test, for which there is an optimal humidity sensor present on the vehicle, and where the optimal humidity sensor is functioning as desired. In some examples, discussed above, more than one suitable object may have been indicated at step 710. In such an example, if it is indicated that a particular ultrasonic sensor is not functioning as desired, then it may be further indicated as to whether a different ultrasonic sensor may be utilized to conduct a relative humidity measurement on the other (e.g. one or more) suitable object(s). In such an example, if another ultrasonic sensor is indicated to be optimally positioned to conduct a relative humidity measurement on another identified suitable object, and it is further indicated that such an ultrasonic sensor is functioning as desired, then it may be determined by the controller to employ the ultrasonic sensor that is functioning as desired to detect the indicated suitable object.

Accordingly, at step 720, responsive to an indication that a particular vehicle ultrasonic sensor is optimally configured to conduct a relative humidity measurement based on a position of an identified suitable object, where the suitable object is identified via one or more onboard cameras, method 700 may proceed to step 725. At step 725, method 700 may include conducting the relative humidity measurement, as described above with regard to the methods depicted in FIGS. 4-6. Method 700 may then end.

As discussed above, certain conditions may trigger a humidity measurement. Furthermore, in some examples, it may be preferable to conduct a humidity measurement utilizing an ultrasonic sensor, whereas in other examples it may be preferable to conduct a humidity measurement using an alternate approach, such as via the use of a universal exhaust gas oxygen (UEGO) sensor. Such an example may include conditions where a vehicle is in operation and one or more onboard camera(s) do not indicate any objects that are stationary with respect to the vehicle (e.g. no other vehicles traveling at essentially the same speed and direction). In another example, optimal conditions for a humidity measurement using a UEGO sensor may be present, such as a deceleration fuel shut off (DFSO) event. In such an example it may be preferable to estimate relative humidity via the UEGO sensor, as will be described in further detail below. By enabling humidity measurements based on vehicle operating conditions, reliable humidity measurements may be obtained at times when it is desirable to obtain humidity measurements.

Turning now to FIG. 8 a schematic view of an example embodiment of an exhaust gas oxygen sensor, such as UEGO sensor 800, configured to measure a concentration of oxygen ($O_2$) in an exhaust gas stream during fueling conditions. In one example, UEGO sensor 800 is an embodiment of UEGO sensor 126 of FIG. 1. It will be appreciated, however, that the sensor of FIG. 8 may alternatively represent an intake oxygen sensor, such as sensor 172 of FIG. 1. The exhaust gas oxygen sensor may also be used during non-fueled conditions to estimate an ambient humidity. Non-fueling conditions may include engine operating conditions in which the fuel supply is interrupted but the engine continues spinning and at least one intake valve and one exhaust valve are operating; such as a deceleration fuel shut off (DFSO) event. Thus, air may be flowing through one or more of the cylinders, but fuel is not injected in the cylinders. Under non-fueling conditions, combustion is not carried out and ambient air may move through the cylinder from the intake passage to the exhaust passage. In this way, a sensor, such as an exhaust gas oxygen sensor, may receive ambient air and ambient humidity may be estimated. In still other examples, an oxygen sensor disposed in the intake air passage (such as oxygen sensor 172 in FIG. 1), and/or a dedicated humidity sensor may be used to estimate ambient humidity during suitable conditions.

Sensor 800 comprises a plurality of layers of one or more ceramic materials arranged in a stacked configuration. In the embodiment of FIG. 8, five ceramic layers are depicted as layers 801, 802, 803, 804, and 805. These layers include one or more layers of a solid electrolyte capable of conducting ionic oxygen. Examples of suitable solid electrolytes include, but are not limited to, zirconium oxide-based materials. Further, in some embodiments such as that shown in FIG. 8, a heater 807 may be disposed in thermal communication with the layers to increase the ionic conductivity of the layers. While the depicted UEGO sensor 800 is formed from five ceramic layers, it will be appreciated that the UEGO sensor may include other suitable numbers of ceramic layers.

The layer 802 includes a material or materials creating a diffusion path 810. The diffusion path 810 is configured to introduce exhaust gases into a first internal cavity 822 via diffusion. The diffusion path 810 may be configured to allow one or more components of exhaust gases, including but not limited to a desired analyte (e.g., $O_2$), to diffuse into the internal cavity 822 at a more limiting rate than the analyte can be pumped in or out by pumping electrodes pair 812 and 814. In this manner, a stoichiometric level of $O_2$ may be obtained in the first internal cavity 822.

The sensor 800 further includes a second internal cavity 824 within the layer 804 separated from the first internal cavity 822 by the layer 803. The second internal cavity 824 is configured to maintain a constant oxygen partial pressure equivalent to a stoichiometric condition, e.g., an oxygen level present in the second internal cavity 824 is equal to that which the exhaust gas would have if the air-fuel ratio was stoichiometric. The oxygen concentration in the second internal cavity 824 is held constant by pumping current $I_{cp}$. Herein, the second internal cavity 824 may be referred to as a reference cell.

A pair of sensing electrodes 816 and 818 is disposed in communication with first internal cavity 822 and the reference cell 824. The sensing electrodes pair 816 and 818 detects a concentration gradient that may develop between the first internal cavity 822 and the reference cell 824 due to an oxygen concentration in the exhaust gas that is higher than or lower than the stoichiometric level.

The pair of pumping electrodes 812 and 814 is disposed in communication with the internal cavity 822, and is configured to electrochemically pump a selected gas constituent (e.g., $O_2$) from the internal cavity 822 through the layer 801 and out of the sensor 800. Alternatively, the pair of pumping electrodes 812 and 814 may be configured to electrochemically pump a selected gas through the layer 801 and into the internal cavity 822. Herein, the pumping electrodes pair 812 and 814 may be referred to as an $O_2$ pumping cell. The electrodes 812, 814, 816, and 818 may be made of various suitable materials. In some embodiments, the electrodes 812, 814, 816, and 818 may be at least partially made of a material that catalyzes the dissociation of molecular oxygen. Examples of such materials include, but are not limited to, electrodes containing platinum and/or gold.

The process of electrochemically pumping the oxygen out of or into the internal cavity 822 includes applying an electric current $I_p$ across the pumping electrodes pair 812 and 814. The pumping current $I_p$ applied to the $O_2$ pumping cell pumps oxygen into or out of the first internal cavity 822 in order to maintain a stoichiometric level of oxygen in the cavity pumping cell. The pumping current $I_p$ is proportional to the concentration of oxygen in the exhaust gas. Thus, a lean mixture will cause oxygen to be pumped out of the internal cavity 822 and a rich mixture will cause oxygen to be pumped into the internal cavity 822.

A control system (not shown in FIG. 8) generates the pumping voltage signal $V_p$ as a function of the intensity of the pumping current $I_p$ required to maintain a stoichiometric level within the first internal cavity 822.

It should be appreciated that the oxygen sensor described herein is merely an example embodiment of a UEGO (or intake manifold oxygen) sensor, and that other embodiments of intake or exhaust oxygen sensors may have additional and/or alternative features and/or designs. As discussed briefly above and which will be described in detail below, under certain conditions it may be preferable to obtain humidity measurements via a UEGO or intake manifold sensor, while in other conditions it may be preferable to obtain humidity measurements via an ultrasonic sensor.

Turning now to FIG. 9 a high level example method 900 for conducting an opportunistic humidity measurement is shown. More specifically, responsive to conditions for a humidity determination procedure being met, a humidity determination may be conducted via either an oxygen sensor, or via the use of an ultrasonic sensor. Method 900 will be described with reference to the systems described herein and shown in FIGS. 1-2 and FIG. 8, and with reference to the methods described herein and shown in FIGS. 4-7, though it should be understood that similar methods may be applied to other systems without departing from the scope of this disclosure. Method 900 may be carried out by a controller, such as controller 12 in FIG. 1, and may be stored at the controller as executable instructions in non-transitory memory. Instructions for carrying out method 900 and the rest of the methods included herein may be executed by the controller based on instructions stored on a memory of the controller and in conjunction with signals received from sensors of the engine system, such as the sensors described above with reference to FIG. 1 and FIG. 8. The controller may employ fuel system actuators such as ultrasonic sensor(s) (e.g. 185), camera(s) (e.g. 186), oxygen sensor(s) (e.g. 126), etc., according to the method below.

Method 900 begins at 902 and may include estimating and/or measuring current vehicle operating parameters. Parameters assessed may include, for example, engine load, engine speed, vehicle speed, manifold vacuum, throttle position, spark timing, EGR flow, exhaust pressure, exhaust air/fuel ratio, assisted or fully-automated parking operations, etc.

Continuing to 905, method 900 may include indicating whether conditions are met for conducting a humidity determination procedure. As discussed above, conditions triggering a humidity measurement may include a change in ambient temperature greater than an ambient temperature threshold, and/or a change in ambient pressure greater than an ambient pressure threshold, where the change in temperature and/or pressure is with respect to a previous (e.g. last, or immediately preceding) humidity measurement. For example, ambient temperature may be directly estimated as the outside air temperature (OAT) from an OAT sensor located on the exterior of the vehicle. In another example, ambient temperature may be inferred based on an air charge temperature (ACT) or an intake air temperature (TAT), as measured by an IAT sensor coupled to an engine intake passage. Ambient pressure may be estimated based on the output of a barometric pressure (BP) sensor coupled to the intake passage. In some examples, instead of an absolute change in temperature or pressure difference, it may be determined if the temperature or pressure has changed by more than a threshold change in percentage (%), wherein the threshold change in percentage may be adjusted based upon the absolute ambient temperature or pressure.

In another example, humidity determination conditions being met may further include a threshold of time of engine operation or distance of vehicle travel greater than a threshold distance since the last humidity measurement.

Other examples where humidity determination conditions may be met may include activation of windshield wipers, a change in weather conditions as indicated by GPS and cross-referenced to the internet, or any other indication that ambient humidity may have changed since the last humidity measurement.

If, at 905 it is indicated that humidity determination conditions are not met, method 900 may proceed to 910. At 910, method 900 may include continuing to adjust vehicle operating parameters based on the last humidity measurement obtained. For example, the last humidity measurement obtained may comprise a humidity measurement conducted via the use of an exhaust gas oxygen sensor, or via an ultrasonic sensor. However, if, at 905 it is indicated that humidity determination conditions are met, method 900 may proceed to 915. At 915, method 900 may include indicating whether conditions are met for determining humidity via either intake or exhaust oxygen sensors.

Conditions being met for a humidity determination via use of an exhaust gas oxygen sensor (e.g. UEGO) may include an engine-non fueling condition, such as a deceleration fuel shutoff (DFSO) event, where an ambient humidity estimate may include alternating between applying first and second voltages to the exhaust gas sensor, and generating an indication of ambient humidity based on sensor outputs at the first and second voltages, as described above with regard to FIG. 8. Alternatively, conditions being met for humidity determination via use of an intake oxygen sensor may include conditions where each of boost, exhaust gas recirculation (EGR), canister purging, and crankcase ventilation, are disabled, and where applying first and second voltages to the intake oxygen sensor may enable an indication of ambient humidity based on sensor output at the first and second voltages, as described above with regard to FIG. 8.

If, at 915, it is indicated that conditions are met for using intake or exhaust gas oxygen sensor(s) for a humidity estimation, then method 900 may proceed to 920. At 920, method 900 may include determining humidity via the intake or exhaust oxygen sensor.

If an exhaust passage UEGO sensor is used for humidity measurement, it may be advisable to wait for a certain specified duration since fuel shut off until the exhaust is substantially free of hydrocarbons from combustion in the engine, before the humidity measurement is commenced. For example, residual gases from one or more previous combustion cycles may remain in the exhaust for several cycles after fuel is shut off and the gas that is exhausted from the chamber may contain more than ambient air for a duration after fuel injection is stopped. In some examples, the duration since fuel shut off may be a time since fuel shut off. In other examples, the duration since fuel shut off may be a number of engine cycles since fuel shut off, for example.

For measuring humidity of the air, the sensor (intake sensor or exhaust sensor) modulates the reference voltage across the pumping cell between a first voltage and a second voltage. Initially, a first (lower) pumping voltage may be applied. As one non-limiting example, the first voltage may be 450 mV. At 450 mV, for example, the pumping current may be indicative of an amount of oxygen in the passage. At this voltage, water molecules may remain intact, thus not contributing towards the total oxygen present in the system. Next, a second (higher) pumping voltage may be applied. As one non-limiting example, the second voltage may be 950 mV. At the higher voltage, water molecules may be dissociated. The second voltage is higher than the first voltage, wherein the second voltage dissociates water molecules and the first voltage does not, and wherein the sensor outputs include a first pumping current generated responsive to applying the first voltage and a second pumping current generated responsive to applying the second voltage. Once the water molecules are dissociated due to the second voltage, the total oxygen concentration increases. The pumping current is indicative of the amount of oxygen in the passage plus an added amount of oxygen from dissociated water molecules. For example, the first voltage may be a voltage at which a concentration of oxygen may be determined, while the second voltage may be a voltage at which water molecules may be dissociated, enabling estimation of humidity.

Accordingly, a change in pumping current during the voltage modulation may next be determined. An indication of ambient humidity may be generated based on a difference between the first and second pumping current generated upon applying the first and second voltages, respectively. The difference (delta) in pumping current at the first reference voltage and the pumping current at the second reference voltage may be determined. The delta pumping current may be averaged over the duration of the DFSO condition (or other condition as described above) such that an ambient humidity may be determined. Once the average change in pumping current is determined, an estimation of ambient humidity may be determined.

Subsequent to estimation of ambient humidity at 920, method 900 may proceed to 925. At 925, method 900 may include adjusting vehicle operating parameters based on the recent humidity measurement. As non-limiting examples, adjusting vehicle operating parameters may include adjusting one or more of an amount of exhaust gas recirculation, an amount of spark advance or retard, a borderline spark value, and a fuel octane estimate. For example, an increase in water concentration of the air surrounding the vehicle may dilute a charge mixture delivered to a combustion chamber of the engine. If one or more operating parameters are not adjusted in response to the increase in humidity, engine performance and fuel economy may decrease and emissions may increase; thus, the overall efficiency of the engine may be reduced. In some embodiments, only one parameter may be adjusted responsive to the humidity. In other embodiments, any combination or sub-combination of these operating parameters may be adjusted in response to measured fluctuations in ambient humidity.

In one example embodiment, an amount of EGR may be adjusted based on the measured humidity. For example, an increase in humidity may be detected by the exhaust gas oxygen sensor during engine non-fueling conditions (or in other examples, by the ultrasonic sensor, as will be discussed below). In response to the increased humidity, during subsequent engine fueling operation, the EGR flow into at least one combustion chamber may be reduced. As a result, engine efficiency may be maintained without degrading NOx emissions. More specifically, a vehicle may be propelled at least in part by an engine comprising an intake manifold and an exhaust manifold, where the engine operates by combustion of fuel provided to the engine, where an amount of exhaust gas recirculated to the intake manifold of the engine is controlled while the engine is operating, and where vehicle operating conditions may be adjusted responsive to an indication of relative humidity, where the adjusting vehicle operating parameters includes one of at least an amount of exhaust gas recirculation provided to the engine, and an amount by which spark provided to the fuel for combustion is retarded or advanced (discussed below).

Responsive to a fluctuation in humidity, EGR flow may be increased or decreased in at least one combustion chamber. As such, the EGR flow may be increased or decreased in only one combustion chamber, in some combustion chambers, or in all combustion chambers. Furthermore, a magnitude of change of the EGR flow may be the same for all cylinders or the magnitude of change of the EGR flow may vary by cylinder based on the specific operating conditions of each cylinder.

In another embodiment, spark timing may be adjusted responsive to the humidity determination. In at least one condition, for example, spark timing may be advanced in one or more cylinders during subsequent engine fueling operation responsive to a higher humidity determination. In another example, spark timing may be scheduled so as to reduce knock in low humidity conditions (e.g., retarded from a peak torque timing), for example. When an increase in humidity is detected via the humidity determination, spark timing may be advanced in order to maintain engine performance and operate closer to or at a peak torque spark timing.

Additionally, spark timing may be retarded in response to a decrease in humidity. For example, a decrease in ambient humidity from a higher humidity may cause knock. If the decrease in humidity is detected by an exhaust gas sensor during non-fueling conditions, such as DFSO, spark timing may be retarded during subsequent engine fueling operation and knock may be reduced. It should be noted that spark may be advanced or retarded in one or more cylinders during subsequent engine fueling operation. Further, the magnitude of change of spark timing may be the same for all cylinders or one or more cylinders may have varying magnitudes of spark advance or retard.

In still another example embodiment, exhaust gas air fuel ratio may be adjusted responsive to the measured ambient humidity during subsequent engine fueling operation. For example, an engine may be operating with a lean air fuel ratio (relative to stoichiometry) optimized for low humidity. In the event of an increase in humidity, the mixture may become diluted, resulting in engine misfire. If the increase in humidity is detected by the exhaust gas sensor during non-fueling conditions, however, the air fuel ratio may be adjusted so that the engine will operate with a less lean air fuel ratio during subsequent fueling operation. Likewise, an air fuel ratio may be adjusted to be a more lean (than stoichiometry) air fuel ratio during subsequent engine fueling operation in response to a measured decrease in ambient humidity. In this way, conditions such as engine misfire due to humidity fluctuations may be reduced. In some examples, an engine may be operating with a stoichiometric air fuel ratio or a rich air fuel ratio. As such, the air fuel ratio may be independent of ambient humidity and measured fluctuations in humidity may not result in an adjustment of air fuel ratio.

Furthermore, as described above, for a vehicle relying on one or more ultrasonic sensor(s) for conducting operations including parking assist, fully automated parking features, or other features, changes in humidity may play a role in the operational use of the ultrasonic sensor. Accordingly, adjusting vehicle operating parameters based on the recent humidity measurement at 925 may further include adjusting a distance detection threshold for the ultrasonic sensor(s). For example, suitable frequencies may be indicated for conducting a distance measurement, where the suitable frequencies are a function of the humidity determination. For example, certain frequencies may be attenuated more greatly as percent relative humidity is increased. Such frequencies may thus be excluded from being utilized for conducting distance measurements, for example. Accordingly, a distance detection threshold for individual frequencies based on the determined ambient humidity may be indicated, and stored in a lookup table at the controller, for example. By adjusting a distance detection threshold for various frequencies of the ultrasonic sensor based on the determined humidity, operational use of the one or more ultrasonic sensor(s) may be improved. Such a concept will be further discussed below with regard to FIG. 11 and FIG. 12.

Furthermore, in some examples, at step 925, tuning detection thresholds may be dynamically adjusted responsive to the indication of humidity. Adjusting tuning detection thresholds may comprise adjusting a voltage level (e.g. voltage response from the ultrasonic sensor) indicative of an object, as compared to noise. More specifically, if tuning detection thresholds are set too high, the sensor may be blind to may objects. Alternatively, if tuning detection thresholds are set too low, the sensor may be overly sensitive to noise, where an object may be indicated where, in fact, there is not object, for example. As humidity may affect attenuation of ultrasonic waves in a frequency-dependent manner, once humidity is known, tuning detection thresholds may be adjusted to account for the variation in attenuation due to the relative humidity. As an example, a tuning detection threshold may be increased (e.g. made more stringent), responsive to an indication of a lower relative humidity (e.g. 20%), whereas the tuning detection threshold may be decreased (e.g. made less stringent), responsive to an indication of higher relative humidity (e.g. 90%). Such examples are meant to be illustrative and are not meant to be limiting. Furthermore, the tuning detection thresholds may be set based on a frequency or frequency(s) selected for detecting objects. More specifically, the tuning detection thresholds may vary as a function of the frequency or frequency(s) selected for detecting objects, and such tuning detection thresholds as a function of frequency may be stored in a lookup table at the controller, for example.

Returning to 915, if conditions are not indicated to be met for using either intake oxygen sensors, or exhaust oxygen sensors, in order to determine ambient humidity, then method 900 may proceed to 930. At 930, method 900 may include determining humidity via one or more ultrasonic sensor(s), as discussed in detail above with regard to FIGS. 4-7. As the methodology for determining humidity via ultrasonic sensors has been previously discussed, for the sake of brevity, the methodology will not be reiterated here. However, it may be understood that any aspects of the methods depicted in FIGS. 4-7 may be utilized in order to determine ambient humidity via the use of ultrasonic sensor(s).

As an example, in some cases, one or more camera(s) may be used in order to identify suitable objects for humidity measurements via an ultrasonic sensor, as described above with regard to FIG. 7. However, there may be cases where a vehicle may not be equipped with a camera. In such an example case, one or more ultrasonic sensors may be systematically tested using the methods described above with regard to FIGS. 4-6, in order to determine ambient humidity. In other words, detecting the presence of an object may be conducted from one or both of: the ultrasonic sensor positioned on the vehicle, and one or more onboard cameras. While not explicitly shown in FIG. 9, it may be understood that if conditions are not met for using intake or exhaust oxygen sensors for determining ambient humidity at step 915, and if subsequent attempts to determine ambient humidity via ultrasonic sensor(s) are not successful (e.g. suitable objects not identified via cameras and/or ultrasonic sensors), then method 900 may be delayed until appropriate conditions are indicated for determining ambient humidity.

Proceeding to step 925, method 900 may include adjusting vehicle operating parameters based on the recent humidity measurement, as determined via the ultrasonic sensor(s). As an extensive description of step 925 is described above, for the sake of brevity the multitude of potential adjustments to vehicle operating parameters as a function of a determined humidity change will not be reiterated here. However, it may be understood that any and all of the vehicle operating parameters adjusted responsive to a humidity determination via intake or exhaust oxygen sensor(s) may additionally be adjusted responsive to humidity determination via one or more ultrasonic sensor(s).

In this way, changes in ambient conditions (e.g., temperature, pressure, etc.) that influence humidity, may be used to trigger humidity measurement, where the humidity measurement may be conducted responsive to vehicle operating conditions such that a likelihood of obtaining an accurate indication of ambient humidity is increased. In other words, by determining vehicle operating conditions responsive to a request for a humidity measurement, an appropriate method of determining humidity may be indicated and carried out according to method 900 depicted in FIG. 9.

In another example, an ultrasonic sensor may be used to adjust vehicle operating conditions, where a knowledge of percent relative humidity may further be advantageous to the adjusting of the vehicle operating conditions. In such an example, ultrasonic sensor(s) may additionally be employed to determine humidity, where vehicle operations are further adjusted based on the humidity measurement. More specifically, a byproduct of diesel fuel combustion is carbon particles, referred to as soot. Emissions control devices, such as diesel particulate filters (DPF) (e.g. 72) reduce soot emissions from an engine by trapping soot particles. Regeneration of the filter may be intermittently conducted, as the filter becomes saturated with soot. For example, the temperature of the filter may be raised to a predetermined level to oxidize or burn the accumulated particulate matter. In some examples, regeneration may be accomplished by injecting additional fuel into an exhaust stream. In other examples, regeneration may be accomplished by altering operation of the engine, such that exhaust temperature is increased. In still other examples, a heater (e.g. 75) may be utilized to selectively heat the DPF. Filter regeneration may occur during normal driving conditions, or may be initiated at other times, such as when a vehicle is stopped, when commanded by a vehicle operator, during servicing of the vehicle, etc. As regeneration involves increasing exhaust temperature, it may be advantageous to conduct such a procedure only if it is indicated that an object is a particular distance from the exhaust.

However, a factor that may contribute to a desired distance of an object from a vehicle exhaust during a DPF regeneration event may include percent relative humidity. For example, heat transfer through air may be a function of ambient temperature and humidity. Thus, if both ambient temperature and humidity are known, thresholds for a distance between an object and an exhaust may be adjusted accordingly, for a particular DPF regeneration event, as will be discussed in greater detail below.

Figure 10:
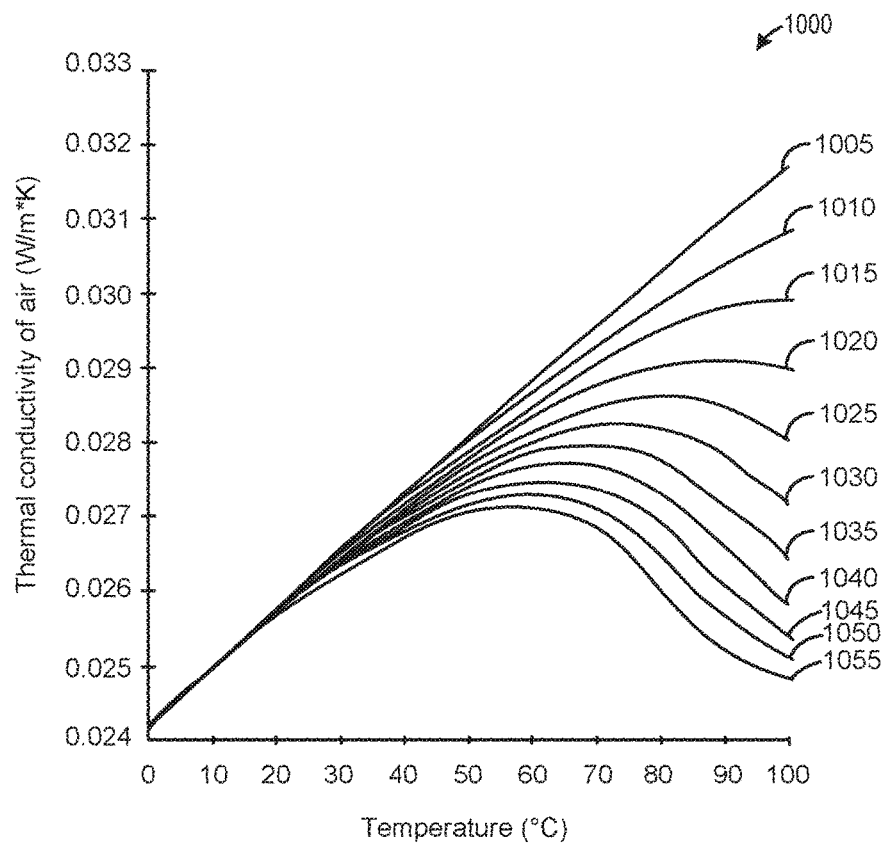
FIG. 10 depicts a graph illustrating thermal conductivity of air as a function of ambient temperature and humidity.

Turning now to FIG. 10, a graph 1000 illustrating a relationship between temperature, humidity, and thermal conductivity of air (in watts per meter kelvin), is shown. More specifically, an x-axis depicts air temperature ranging from 0° C. to 100° C., and a y-axis depicting thermal conductivity of air ranging from 0.024 W/m*K to 0.033 W/m*K, is shown. Furthermore, various plots illustrating percent humidity are shown. More specifically, plot 1005 illustrates 0% humidity, plot 1010 illustrates 10% humidity, plot 1015 illustrates 20% humidity, plot 1020 illustrates 30% humidity, plot 1025 illustrates 40% humidity, plot 1030 illustrates 50% humidity, plot 1035 illustrates 60% humidity, plot 1040 illustrates 70% humidity, plot 1045 illustrates 80% humidity, plot 1050 illustrates 90% humidity, and plot 1055 illustrates 100% humidity. As illustrated, thermal conductivity of air is a function of temperature and humidity. For example, thermal conductivity of air at 100% humidity increases from 0° C. to about 60° C. However, if the temperature is increased further, thermal conductivity decreases. Thus, because thermal conductivity is a function of temperature and ambient humidity, if both variables (temperature and ambient humidity) are known, then thermal conductivity of air may be determined, and a threshold for a distance between an exhaust and an identified object may be adjusted accordingly, as will be described in detail according to the method depicted in FIG. 11.

Figure 11:
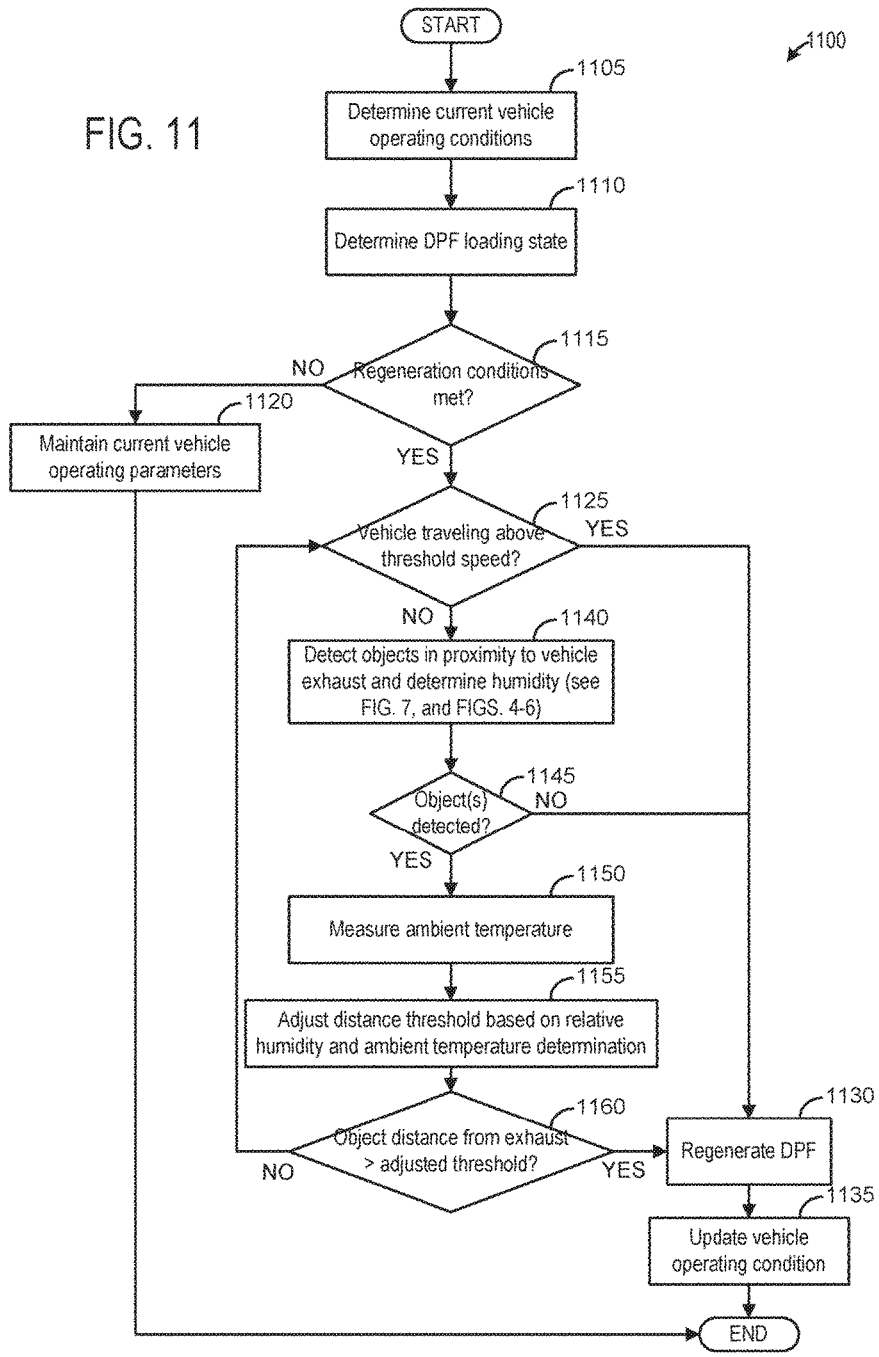
FIG. 11 shows a high level example method for conducting a diesel particulate filter regeneration procedure, based on whether an object is detected positioned in an area close to a vehicle exhaust.

Turning now to FIG. 11, a high level example method for conducting a DPF regeneration procedure, is shown. More specifically, responsive to conditions being met for DPF regeneration, and where a vehicle speed is indicated to be below a threshold speed, objects in proximity to a vehicle exhaust and their distance from the exhaust may be determined, and ambient humidity and ambient temperature indicated. Based on the indicated distance of objects in proximity to the exhaust, and further based on the indicated ambient humidity and temperature, a distance threshold may be adjusted such that, if an object is positioned at a distance from the exhaust less than the adjusted threshold distance, regeneration of the filter may be postponed until more favorable conditions for DPF regeneration are met. Said another way, the method depicted in FIG. 11 includes regenerating a particulate filter coupled to an underbody of the motor vehicle by causing burning of particulate stored in the particulate filter resulting in hot gases exiting a rear of the motor vehicle; selecting the selected sensor based on a transmission path of the selected sensor overlapping at least a portion of the hot gases exiting the rear of the motor vehicle; and postponing or aborting the regeneration based on there being an object within a predetermined distance of the hot gases exiting the rear of the motor vehicle. As one example the method may further include measuring an air temperature near where the hot gases exit the rear of the motor vehicle; determining thermal conductivity of air based, at least in part, on the indication of relative humidity and the air temperature; and adjusting a distance threshold for the regeneration procedure, where the adjusting the distance threshold includes decreasing the distance threshold as thermal conductivity decreases, and increasing the distance threshold as thermal conductivity increases.

Method 1100 will be described with reference to the systems described herein and shown in FIG. 1, though it should be understood that similar methods may be applied to other systems without departing from the scope of this disclosure. Method 1100 may be carried out by a controller, such as controller 12 in FIG. 1, and may be stored at the controller as executable instructions in non-transitory memory. Instructions for carrying out method 1100 and the rest of the methods included herein may be executed by the controller based on instructions stored on a memory of the controller and in conjunction with signals received from sensors of the engine system, such as the sensors described above with reference to FIG. 1. The controller may employ vehicle system actuators such as ultrasonic sensor(s) (e.g. 185), camera(s), a hydrocarbon (HC) reductant delivery system (e.g. 74), fuel injector(s) (e.g. 66), DPF heater (e.g. 75), etc., according to the method below.

Method 1100 begins at 1105 and may include determining current vehicle operating conditions. Operating conditions may be estimated, measured, and/or inferred, and may include one or more vehicle conditions, such as vehicle speed, vehicle location, etc., various engine conditions, such as engine status, engine load, engine speed, A/F ratio, etc., various fuel system conditions, such as fuel level, fuel type, fuel temperature, etc., various evaporative emissions system conditions, such as fuel vapor canister load, fuel tank pressure, etc.

Proceeding to 1110, method 1100 may include determining a loading state of a diesel particulate filter (DPF) (e.g. 72). Various strategies may be used to determine a loading state of the DPF in order to indicate whether the DPF filter may need to be regenerated. For example, a threshold pressure difference across the DPF may be indicative of a loading state of the DPF above a threshold loading state. In such an example, one pressure sensor (e.g. 80) may be positioned upstream of the DPF, and another pressure sensor (e.g. 82) may be positioned downstream of the DPF, such that a pressure differential across the DPF may be communicated to the vehicle controller. In other examples, loading state of the DPF may be inferred or estimated as a function of a number of miles the vehicle has been driven since a previous DPF regeneration procedure. In a still further example, loading state of the DPF may be inferred or estimated as a function of a duration of engine operation since a previous DPF regeneration procedure. Such examples are meant to be illustrative and in no way limiting. For example, other methods of indicating DPF loading state known in the art may be utilized, without departing from the scope of this disclosure.

Proceeding to 1115, it may be indicated whether conditions are met for conducting a DPF regeneration procedure. For example, if a DPF loading state is indicated to be above the predetermined threshold, as discussed above with regard to step 1110 of method 1100, then it may be indicated that DPF regeneration conditions are met. However, if DPF regeneration conditions are not met, method 1100 may proceed to 1120. At 1120, method 1100 may include maintaining current vehicle operating parameters. For example, at 1120, method 1100 may include continuing non-DPF-regeneration engine operation, and the DPF may continue to collect soot and monitor the DPF loading state.

Returning to 1115, if regeneration conditions are indicated to be met, method 1100 may proceed to 1125, and may include indicating whether the vehicle is traveling above a predetermined velocity threshold. For example, the predetermined velocity threshold may be a predetermined threshold velocity at which convection from external environmental air may be sufficient to reduce exhaust gas outlet temperatures below a threshold temperature. In such an example, potential issues with objects being positioned close to the exhaust may be disregarded, as exhaust temperatures are not likely to pose a significant issue due to the reduction in exhaust gas outlet temperatures due to air flow. Furthermore, as the vehicle is traveling at a velocity greater than the predetermined velocity threshold, likelihood of an object being positioned close to the exhaust may additionally be low so as not to pose a significant concern. Accordingly, if at 1125 it is indicated that the vehicle is traveling above the predetermined velocity threshold, method 1100 may proceed to 1130, and may include conducting the regeneration procedure without determining whether an object is within a predetermined distance of the hot gases exiting the rear of the motor vehicle.

Regenerating the DPF at 1130 may include adjusting engine operating parameters such that the DPF may be regenerated. For example, the engine controller may include stored instructions for regenerating the DPF. Examples may include operating a heater (e.g. 75) coupled to the DPF, or by raising a temperature of engine exhaust (e.g. by operating rich, or direct injection of fuel into exhaust gas), where the raised engine exhaust gas may serve to raise DPF temperature to convert soot in the DPF to ash.

Regeneration of the DPF at 1130 may further include determining whether soot load is lower than a predetermined threshold. For example, the predetermined threshold may include a lower threshold below which regeneration of the DPF may be terminated. Regeneration may be maintained, until soot load is lower than the predetermined threshold, for example. In such an example, a loading state of the DPF may be indicated via, for example, a pressure differential across the DPF. However, as discussed above, other methods of indicating DPF loading state may be utilized without departing from the scope of this disclosure.

If the DPF load is sufficiently low (e.g. below the predetermined threshold), then regeneration of the DPF may be terminated. Termination may include discontinuing any vehicle operating parameter contributing to the heating of the filter. For example, if fuel was being injected into the exhaust gas, such injection may be terminated. In another example, if fuel injection to the engine was commanded rich, such fuel injection may similarly be discontinued and fuel injection returned to default operation, where default operation may include an operational state prior to conducting the DPF regeneration procedure. In still other examples, if a heater was activated in order to regenerate the DPF, then the heater may be deactivated. In all such examples, the actions may be controlled by a vehicle controller (e.g. 12), where by signals are sent to the various actuators (e.g. fuel injectors, heater) to terminate the regeneration operation.

Continuing at 1135, method 1100 may include updating vehicle operating conditions. For example, a loading state of the DPF may be updated based on the recent DPF regeneration procedure. Such updated information may be stored at the controller, for example. Furthermore, based on the regeneration procedure and subsequent DPF loading state, a regeneration schedule stored at the controller may be updated. For example, in a case where a regeneration schedule includes requesting a regeneration procedure after a predetermined number of miles driven, or after a predetermined number of hours of engine operation, such numbers may be reset at the controller in order to effectively request a future regeneration procedure. Method 1100 may then end.

Returning to 1125, if the vehicle is not indicated to be traveling above the predetermined threshold speed, then method 1100 may proceed to 1140. At 1140, method 1100 may include detecting objects in proximity to the vehicle exhaust, and may further include determining relative humidity, if possible. For example, if the vehicle is equipped with one or more rear-facing cameras, such camera(s) may be commanded by the controller to search an area at the rear of the vehicle. Such an example methodology for utilizing available onboard camera(s) in order to detect objects, and where, responsive to detection of suitable object, relative humidity may be determined, is depicted above in the methods illustrated in FIGS. 7, and 4-6. In a case where determining humidity is possible, it may be understood that ambient temperature may additionally be determined, as discussed above with regard to FIGS. 4-6. Furthermore, it may be understood that an ultrasonic sensor may be selected for determining relative humidity, where the ultrasonic sensor is selected from a plurality of sensors based on the selected sensor transmission and receipt path overlapping at least a portion of the hot gases exiting the rear of the motor vehicle.

Exhaustive description of how one or more camera(s) may be utilized to detect objects that may be in a position close to the exhaust will not be reiterated here, as it has been discussed above. Briefly, the one or more camera(s) may be commanded by the controller to search for objects at the rear of the vehicle that may be in close proximity to the exhaust. If such objects are detected, it may be further indicated, as discussed above, as to whether the objects appear to be stationary with respect to the vehicle, whether the vehicle is moving or is parked. For example, multiple camera images may be obtained, where if objects are indicated to change position, size, or shape, between images, then it may be determined that such an identified object may not be stationary with respect to the vehicle. In some examples, ultrasonic sensors may additionally or alternatively be used to identify objects, and to indicate whether the identified objects appear to be stationary with respect to the vehicle.

If, based on the one or more rear-facing camera(s) (or ultrasonic sensors), potential objects are indicated that may be stationary with respect to the vehicle (e.g. moving car traveling at the same speed and direction as the vehicle attempting to conduct a DPF regeneration procedure), humidity may further be determined, according to the methods described above in FIGS. 4-6. As discussed above, it may be understood that the ultrasonic sensor may be selected for use in conducting a humidity determination based on the ultrasonic signals overlapping at least a portion of the hot gases exiting the rear of the vehicle. Furthermore, in determining ambient temperature, a temperature sensor may be selected that is in close proximity to the vehicle exhaust.

Some examples may include a vehicle that is not traveling, but rather is stationary (e.g. parked). In some examples, parked regeneration may include a vehicle operator putting a vehicle transmission (not shown) in neutral, applying a parking break (not shown), pressing and releasing a clutch pedal (not shown), and pressing and holding a regeneration button on a vehicle dashboard until RPMs increase, and wherein the DPF regeneration procedure may commence. In such an example, when the regeneration is complete, lights on the dashboard may go out, indicating completion of the regeneration event. While the vehicle is parked, it may be likely that the one or more rear-facing camera(s) and/or ultrasonic sensors may detect one or more objects in a proximity to the exhaust, and where an accurate measurement of humidity may be obtained, as discussed above and according to the methods depicted above with regard to FIGS. 4-6.

As discussed above, because humidity may have an effect on operational use of an ultrasonic sensor, by determining relative humidity, it may be possible to adjust (correct) a distance detection threshold for the ultrasonic sensor being used to determine distance between the vehicle and an object of interest. For example, because certain frequencies may be differentially attenuated as a function of relative humidity, a distance detection threshold for individual frequencies based on the determined relative humidity may be indicated, and stored in a lookup table at the controller (e.g. 12). For example, at high humidity indications, frequencies in a lower range (20-40 kHz) may be utilized, instead of higher frequencies, such that operational use of the ultrasonic sensor may be improved.

Furthermore, in attempting to detect objects in proximity to the vehicle exhaust, only those one or more ultrasonic sensors configured on the vehicle for detecting objects to the rear of the vehicle may be employed for determining relative humidity and detecting objects at 1140.

In some examples, a vehicle may not be equipped with one or more rear-facing camera(s). In such an example, one or more ultrasonic sensors positioned at the rear of the vehicle may be commanded to conduct a relative humidity estimate, and a distance measurement, according to the methods described above and illustrated in FIGS. 4-6. For example, ultrasonic sensors may be used in lieu of cameras to detect objects in proximity to the exhaust. Ultrasonic sensors may further be used to detect objects that appear stationary with respect to the vehicle (e.g. indicated via the same transit time between two or more ultrasonic frequencies), such that a humidity measurement may be obtained, and an accurate distance measurement may thus be conducted.

Proceeding to 1145, if no objects were detected, method 1100 may proceed to 1130, and may include regenerating the DPF, as described in detail above. However, if objects were detected and, where possible, if an estimate of humidity was determined, then method 1100 may proceed to 1150.

As discussed above, thermal conductivity of air may be a function of air temperature and relative humidity. Accordingly, responsive to objects being detected and a humidity measurement being conducted, method 1100 may include measuring ambient temperature at 1150. As discussed above, measuring ambient temperature may be conducted via an outside air temperature (OAT) sensor (e.g. 127). Such an indication of outside air temperature may be stored at the controller (e.g. 12), for example. With an object detected, and with relative humidity (where possible) and ambient air temperature determined, method 1100 may proceed to 1155. At 1155, method 1100 may include adjusting a distance threshold based on the relative humidity measurement and ambient temperature determination, where air temperature is measured near where hot gases exit the rear of the motor vehicle. For example, the distance threshold may comprise a distance that, above which a DPF regeneration procedure may be conducted without concern that heat from the exhaust may adversely impact the detected object (or objects). In a case where humidity was not able to be determined, rather than adjusting the distance threshold, a predetermined distance threshold may instead be utilized.

More specifically, as illustrated in FIG. 10, thermal conductivity of air may fluctuate as a function of humidity, and temperature. As an example, at 60° C. and 80% humidity (e.g. line 1045), thermal conductivity of air may be ~0.0275 W/m*K, whereas at 90° C. and 80% humidity, thermal conductivity of air may be ~0.026. In other words, thermal conductivity may decrease as temperature increases from 60° C. to 90° C. when ambient humidity is at 80%. Thus, heat may not be conducted as efficiently in air as temperature increases from 60° C. to 90° C. under conditions where ambient humidity is 80%. Accordingly, method 1100 may include adjusting the distance threshold for the regeneration procedure, where the adjusting the distance threshold includes decreasing the distance threshold as thermal conductivity decreases, and increasing the distance threshold as thermal conductivity increases.

Such conditions are meant to be illustrative, but it may be understood that the distance threshold may be adjusted accordingly based on any relative humidity measurement and temperature measurement, according to the graph 1000 depicted in FIG. 10. In one example, a lookup table may be stored at the controller, where the lookup table may include an amount whereby the distance threshold may be adjusted based on indicated relative humidity and temperature. As such, for any given pair of relative humidity and temperature measurements, an amount whereby the distance threshold may be adjusted may be readily obtained. Importantly, by using the ultrasonic sensor to detect both ambient humidity and distance between the sensor and the indicated object, accuracy of the adjusting of the distance threshold may be increased, as compared to a condition where ambient humidity may be inferred from another means (e.g. intake or exhaust oxygen sensors). More specifically, because humidity may be localized, obtaining humidity via the use of ultrasonic sensors just prior to adjusting the distance threshold may be advantageous in that humidity may be accurately determined specifically for the purpose of adjusting the distance threshold. Furthermore, because the ultrasonic sensor for determining humidity may be selected based on at least a portion of the transmission and receipt path of the ultrasonic sensor overlapping the hot gases exiting the rear of the motor vehicle, humidity determination results may specifically reflect humidity conditions near the rear of the vehicle where hot gases are expected during the DPF regeneration procedure.

After adjusting the distance threshold as a function of determined ambient humidity and temperature at 1155, method 1100 may proceed to 1160. At 1160, method 1100 may include indicating whether distance between the object of interest and the exhaust is greater than, or less than, the adjusted distance threshold. For example, the ultrasonic sensors may be utilized to determine a distance of the indicated object from the exhaust. If the object is indicated to be positioned less than the adjusted distance threshold away from the exhaust, method 1100 may include returning to step 1125, and may include continuing to determine whether conditions are present for conducting the DPF regeneration procedure. However, if the object is indicated to be positioned greater than the adjusted distance threshold away from the exhaust, method 1100 may proceed to 1130, and may include regenerating the DPF filter, as described in detail above.

While not explicitly illustrated in FIG. 11, it may be understood that while the DPF is being regenerated, one or more of the onboard camera(s) and ultrasonic sensor(s) may be utilized in order to ensure that an object does not cross the adjusted distance threshold while the DPF regeneration is taking place. For example, the one or more camera(s) may be commanded by the controller to record images over the course of the DPF regeneration event, and process the images as discussed above using object recognition algorithms stored at the controller, such that it may be indicated whether any objects appear to have moved during the regeneration event, and importantly, whether the objects appear to have moved to a position that may be less than the adjusted distance threshold away from the vehicle exhaust. Such examples may include determining the distance between the exhaust and the identified objects, via the ultrasonic sensor(s), for example. In a case where one or more cameras may not be included in the vehicle, then the ultrasonic sensor(s) may be utilized solely to determine distance of the identified object(s) from the vehicle exhaust. In an example case where it is determined that an object or objects are positioned below the adjusted distance threshold, then the regeneration event may be abruptly terminated, or suspended. Such an action may be carried out by the controller, for example. By monitoring the DPF regeneration event via the use of one or more camera(s) and ultrasonic sensor(s), the presence of an object at a position less than the adjusted distance threshold may be readily identified, such that the DPF regeneration event may be suspended. Said another way, method 1100 may include conducting the regeneration procedure responsive to the object being positioned at a greater distance than the threshold distance; monitoring the object and an area proximate the rear of the vehicle via the one or more cameras during the regeneration procedure; and terminating the regeneration procedure if the object or other object is identified as being closer than the threshold distance during the regeneration procedure.

As discussed above, by indicating ambient temperature and ambient humidity, two noise factors for ultrasonic sensors, a distance detection threshold may be adjusted such that operational use of the ultrasonic sensor may be improved. However, it may be further desirable to select optimal frequencies for particular distance measurements, provided there is an indication of whether an object of interest may be a short distance (short range) away, a medium distance (medium range) away, or a long distance (long range) away from the ultrasonic sensor. By using an optimal frequency for a particular distance measurement, where a distance detection threshold has been adjusted, operational use of the ultrasonic sensor may be still further improved. In some examples, the optimal frequency may be a function of the adjusted distance detection threshold, and the desired operational use of the sensor. In some examples, a plurality of images of an environment proximal to the vehicle may be captured via one or more onboard cameras, where the desired operational use of the sensor is at least partially determined via the one or more cameras, as will be discussed in further detail below.

Figure 12:
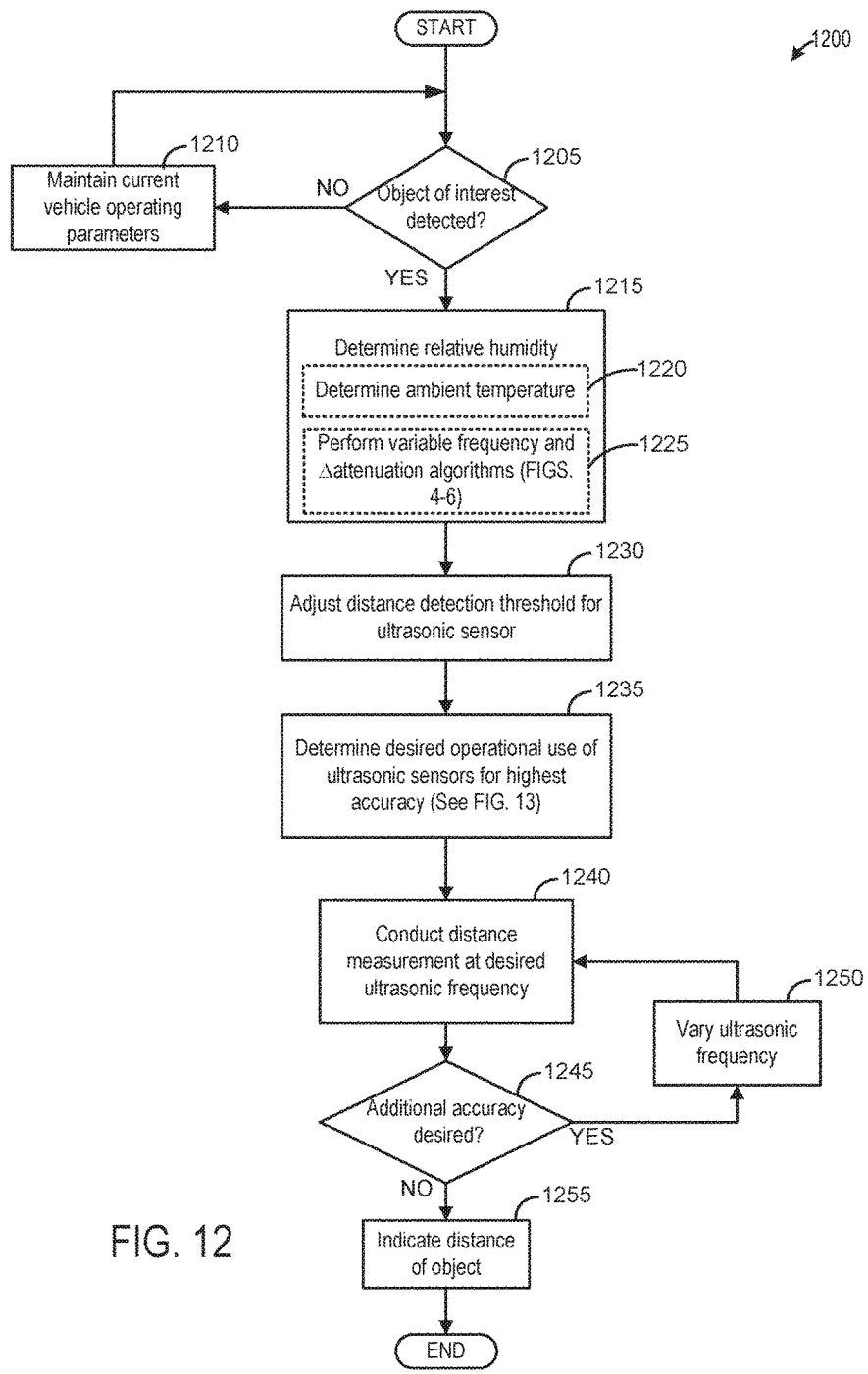
FIG. 12 shows a high level example method for adjusting a distance detection threshold for an ultrasonic sensor.

Turning now to FIG. 12, a high level example method for adjusting a distance detection threshold for an ultrasonic sensor and further determining optimal frequency(s) for distance measurements, is shown. More specifically, by determining ambient humidity and ambient temperature, two noise factors for ultrasonic distance measurements may be controlled for, such that a distance detection threshold for the ultrasonic distance measurement may be adjusted. As a function of the adjusted distance detection threshold, optimal frequency(s) for a subsequent distance determination may be selected. In some examples, the same ultrasonic sensor used to conduct the humidity determination may be subsequently used to conduct a distance measurement. However, in other examples, the sensor used to determine relative humidity may be a different sensor.

Method 1200 will be described with reference to the systems described herein and shown in FIG. 1, though it should be understood that similar methods may be applied to other systems without departing from the scope of this disclosure. Method 1200 may be carried out by a controller, such as controller 12 in FIG. 1, and may be stored at the controller as executable instructions in non-transitory memory. Instructions for carrying out method 1200 and the rest of the methods included herein may be executed by the controller based on instructions stored on a memory of the controller and in conjunction with signals received from sensors of the engine system, such as the sensors described above with reference to FIG. 1. The controller may employ fuel system and evaporative emissions system actuators, such as ultrasonic sensor(s) (e.g. 185), camera(s) (e.g. 186), etc., according to the method depicted below.

Method 1200 begins at 1205 and may include indicating whether an object of interest has been detected. As discussed above with regard to FIG. 7, detecting and indicating objects of interest may in some examples be conducted via one or more onboard camera(s). As a procedure for detecting objects via one or more camera(s) has been thoroughly discussed above, for brevity, a full description will not be reiterated here. However, it may be understood that at 1205, object detection and indication of suitable objects may be determined via one or more camera(s) as discussed above at FIG. 7. In some examples, a vehicle may not be equipped with one or more camera(s), or the vehicle may be equipped with camera(s) but not necessarily in optimal position for detecting all potential objects positioned around the vehicle. In such an example, one or more ultrasonic sensor(s) may additionally or alternatively be utilized in order to detect and indicate potential suitable objects of interest. In some examples, an object search may be initiated based on humidity determination conditions being met, such as an indicated change in ambient temperature or pressure, described above at step 905 of method 900. In another example, suitable objects may be detected while a vehicle is performing an assisted, or fully automated, parking procedure. Such examples and meant to be illustrative, and are not meant to be limiting.

If, at 1205, no suitable objects of interest are indicated, method 1200 may proceed to 1210 and may include maintaining current vehicle operating parameters. For example, if the controller was commanded to search for suitable objects of interest via camera(s) and/or ultrasonic sensor(s), then at 1205, method 1200 may continue searching for the suitable objects of interest.

Alternatively, if at 1205 method 1200 indicates that a suitable object of interest may be identified, method 1200 may proceed to 1215. At 1215, method 1200 may include determining humidity, via the use of an ultrasonic sensor, as described above. More specifically, determining humidity may include determining ambient temperature at 1220, via, for example, an OAT sensor (e.g. 127). Furthermore, determining ambient humidity may additionally include performing the variable frequency algorithm (FIG. 5) and delta attenuation calculation (FIG. 6). In other words, determining ambient humidity at 1215 may comprise determining humidity according to the high level method of FIG. 4. Because the method for determining humidity via the use of an ultrasonic sensor has been described in detail above, for brevity an in-depth explanation will not be reiterated here. However, it may be understood that determining ambient humidity at 1215 may be accomplished via following the method depicted in FIG. 4.

Responsive to humidity (and ambient temperature) being determined, method 1200 may proceed to 1230. At 1230, method 1200 may include adjusting a distance detection threshold for the ultrasonic sensor that was utilized to make the humidity determination. For example, a maximum range at which an ultrasonic sensor can detect a target object may be affected by attenuation of sound, where a major noise factor in terms of sound attenuation may comprise ambient humidity. Furthermore, an accurate determination of the speed of sound may be important for converting a transit time from sending to receipt of an ultrasonic signal into a distance measurement. As the speed of sound is influenced by ambient temperature, knowledge of the ambient temperature may further increase operational use of the ultrasonic sensor. Furthermore, accurate estimation of ambient humidity may necessitate a knowledge of ambient temperature, as discussed above. Accordingly, at 1230, adjusting the distance detection threshold may be based on the indicated humidity and ambient temperature. In some examples, the distance detection threshold may be frequency dependent, such that the distance detection threshold may be different for different frequencies. As an example, a distance measurement greater than a particular distance may not be achievable at 100 kHz, at a relative humidity percentage of 80%, but may be achievable instead via the use of 30 kHz, due to a reduction in attenuation of sound at 30 kHz as compared to 100 kHz at 80% humidity. Such an example is meant to be illustrative. Accordingly, responsive to determination of humidity, distance detection threshold(s) at various frequencies, for the indicated humidity, may be determined and stored in a lookup table, for example. Said another way, in some examples, adjusting the distance detection threshold for the ultrasonic sensor responsive to an indication of relative humidity may include indicating suitable frequencies for conducting distance measurements, as a function of the indication of relative humidity.

Proceeding to 1235, method 1200 may include determining desired operational use of the ultrasonic sensor, such that the sensor may be used to conduct a distance measurement based on the desired operational use of the sensor. More specifically, determining desired operational use may comprise determining whether a particular object for which a distance determination is desired is located at a short range (e.g. less than 1 meter), at a medium range (e.g. greater than one meter but less than 2 meters), or at a long range (e.g. greater than 2 meters). In one example, determining a range for which a particular object is positioned away from the ultrasonic sensor may include estimating a distance (range) via the use of the one or more onboard camera(s), if equipped. For example, via the use of object recognition software commonly known in the art, algorithms for which may be stored at the controller, a rough distance estimation may be obtained simply via the use of the onboard cameras. In another example, a rough calculation may be indicated by initial ultrasonic sensor distance determination. In such an example, because the distance to the object is not known, one or more particular frequency(s) may be sent and received by the ultrasonic sensor in order to make a rough distance determination calculation. Such a calculation may include determining whether the distance between the ultrasonic sensor and the object of interest is a short range, medium range, or long range, away from the sensor.

Accordingly, at 1235, determining desired operational use of ultrasonic sensors may include retrieving information from a lookup table stored at the controller, for example the lookup table depicted in FIG. 13.

Turning to FIG. 13, an example lookup table is depicted, illustrating an optimal ultrasonic frequency that may be used for distance measurements, responsive to the object of interest being indicated to be positioned at a short range, medium range, or long range away from the ultrasonic sensor used for conducting the distance measurement. As will be discussed below, the desired frequency(s) to use may be further selected as a function of the adjusted distance detection thresholds, described above.

As one example, if the desired distance of an object of interest is indicated to be positioned at a short range away from the ultrasonic sensor, then all frequencies that the ultrasonic sensor is capable of transmitting (e.g. 20 kHz to 100 kHz), may in theory be utilized for a distance measurement, as sound attenuation may not play a large role at short range. However, based on the distance detection threshold, some frequencies may still be desired over others. In any case, for short range distance measurements, because most if not all frequencies may provide accurate distance measurements due to little effect of sound attenuation, the frequency that may be chosen may comprise an optimal frequency that the piezoelectric crystal of the ultrasonic sensor was designed to operate at. For example, this frequency may be a known value, and may be stored at the controller. If, based on the adjusted distance detection threshold, such a frequency is not desirable due to potential attenuation at such a frequency, then a lower frequency may be selected, for example.

As another example, if the desired distance of an object of interest is indicated to be positioned at a medium range away from the ultrasonic sensor, then frequencies in a low to middle range (e.g. 20 kHz to 50-60 kHz) may be selected to conduct the distance measurement for increased accuracy. In such an example, if the adjusted distance detection threshold excludes any of the potential frequencies from being used, then frequencies other than those excluded frequencies may be selected. For example, at 60 kHz, sound attenuation due to a particular relative humidity may result in objects not being able to be accurately detected (e.g. distance measurement not accurate) at 1.5 meters away from an ultrasonic sensor, but other lower frequencies may enable accurate detection and measurement. Such an indication may be provided via the adjusted distance detection lookup table, described above with regard to step 1230 of method 1200. In any case, whether certain frequencies in the low to middle range may be excluded based on the adjusted distance detection threshold or not, a frequency may be chosen such that the frequency chosen is within the range for optimal accuracy, and which is closest to the optimal frequency that the sensor was designed to operate at. As discussed above, such an indication of optimal frequency may be stored at the controller.

As a still further example, if the desired distance of an object of interest is indicated to be positioned at a long range away from the ultrasonic sensor, then low frequency operation (e.g. between 40 kHz and 20 kHz) may be selected to conduct the distance measurement for increased accuracy. As discussed above, if the adjusted distance detection threshold excludes any of the potential frequencies from being used, then frequencies other than those excluded may be selected. Similar to that described above for the medium range, whether certain frequencies are excluded or not, a frequency may be chosen such that the frequency chosen is within the range for desired operation, and which is closest to the optimal frequency that the sensor was designed to operate at.

Returning to 1235, responsive to determining desired operational use of the ultrasonic sensor, method 1200 may proceed to 1240. At 1240, method 1200 may include conducting the distance measurement, or measurements, via sending and receiving the ultrasonic wave frequency chosen as an optimal frequency at step 1235. As discussed above, the controller may command an oscillating voltage to be sent to the ultrasonic sensor, thus converting electrical oscillation into mechanical sound waves that may be transmitted from the ultrasonic sensor. After being reflected from the object of interest, the sound waves may be received by the sensor (e.g. receiver), where receiving the sound waves involves converting the mechanical waves back to electrical oscillations that may be interpreted by the controller. Based on the transit time from transmission to receipt of the reflected waves, a distance measurement may be indicated. More specifically, as discussed above, distance may be indicated based on the formula $d=t*c/2$, where c is the speed of sound and t is the transit time.

Furthermore, at 1240, tuning detection thresholds may additionally be adjusted responsive to the indication of humidity. As discussed above, adjusting tuning detection thresholds may comprise adjusting a voltage level for indication of an object, as compared to noise, via the one or more ultrasonic sensor(s). The tuning detection thresholds may vary as a function of the frequency or frequency(s) selected for detecting objects, and such tuning detection thresholds as a function of frequency may be stored in a lookup table at the controller, for example.

In some examples, there may be instances where the chosen (selected) frequency for conducting the distance measurement results in a signal-to-noise issue, for one reason or another. For example, an angle of the object of interest may have changed, or the object may have moved from one distance to another, etc. Accordingly, proceeding to 1245, method 1200 may include indicating whether additional accuracy may be desired. If attenuation or some other environmental effect resulted in a signal-to-noise issue during conducting the distance measurement, such that a desired distance estimate may not be obtained, then method 1200 may proceed to 1250. At 1250, method 1200 may include actions such as varying the ultrasonic frequency in an attempt to obtain improved distance measurements between the ultrasonic sensor and the object of interest. For example, if a specific frequency was selected based on the object being a middle range distance away from the sensor, then other frequencies corresponding to optimal middle range distance determination may be next utilized. In some examples, one or more camera(s) (if the vehicle is equipped) may be utilized in order to indicate whether the object of interest may have moved (e.g. moved away or moved closer to or further from the ultrasonic sensor). In still other examples, frequencies outside of the chosen range may be utilized, in an attempt to increase the accuracy of the distance measurement. For example, if the object of interest was predicted to be at a middle range distance, and thus a frequency of 50 kHz was selected, then if a good distance estimate was not obtained, a lower frequency (e.g. 30 kHz) may next be utilized, in an attempt to reduce attenuation. Such examples are illustrative and are not meant to be limiting.

Returning to 1245, if additional accuracy is not desired, in other words, if signal-to-noise of the transmitted and received ultrasonic sound wave is above a level where desired distance measurement(s) may be obtained, then method 1200 may continue to 1255, and may include indicating the distance of the object. Such a distance determination may be at least temporarily stored at the controller, in one example. Furthermore, in some examples, such distance determination methodology may be utilized in order to more effectively carry out an assisted or fully automated parking maneuver, such as according to the system described above with regard to FIG. 2.

Turning now to FIG. 14, an example timeline 1400 depicting conducting an opportunistic humidity determination procedure, using the methods depicted in FIGS. 4-7, and FIG. 9 is shown. Timeline 1400 includes plot 1405, indicating whether humidity determination conditions are met, over time. Timeline 1400 further includes plot 1410, indicating whether a vehicle engine is on, or off, over time. Timeline 1400 further includes plot 1415, indicating whether an object detection procedure has been initiated, over time. Timeline 1400 further includes plot 1420, indicating whether humidity has been determined, over time. Timeline 1400 further includes plot 1425, indicating an amount of exhaust gas recirculation (EGR) being provided to engine intake, over time. Timeline 1400 further includes plot 1430, indicating relative humidity, over time.

At time t0, the vehicle is in operation, being propelled via an engine, illustrated by plot 1410. Furthermore, humidity determination conditions are not indicated to be met at time t0. As discussed above, conditions for a humidity determination procedure being met may include an indication of an ambient temperature change greater than a temperature threshold and/or a change in ambient pressure greater than a pressure threshold since previous (e.g. last, or immediately preceding) humidity determination. Further conditions for a humidity determination procedure being met may include a threshold time of engine operation, or distance of vehicle travel greater than a threshold distance since a last humidity measurement, or a change in weather conditions indicated by other means, such as via GPS and cross-referenced to the internet, etc.

As the vehicle is in operation and the humidity determination conditions have not been indicated to be met at time t0, in this example illustration object detection via, for example, camera(s) and/or ultrasonic sensor(s) is not indicated to be initiated. However, there may be some circumstances where humidity determination conditions are not met, yet object detection may still be initiated. Such examples may include a vehicle conducting a parking event, where camera(s) and/or onboard ultrasonic sensor(s) may be employed to assist the parking operation, for example.

Furthermore, humidity is not indicated to have been determined since a previous humidity measurement, indicated by plot 1420. As such, it may be understood that "no" with regard to plot 1420 may refer to a situation where humidity has not been determined since a previous humidity measurement, and wherein a current humidity measurement being determined may be indicated by "yes" with regard to plot 1420.

Finally, at time t0, a determined amount of exhaust gas is being recirculated to the intake of the vehicle engine, where an amount of EGR may be at least partially determined by a last, or previous humidity measurement. With regard to plot 1425, "+" may refer to increasing amounts of EGR, while "−" may refer to decreasing amounts of EGR. Furthermore, N/A may refer to a condition where no EGR is being recirculated to the engine intake, such as when the engine is not operating, for example.

At time t1, humidity conditions are indicated to be met. Accordingly, it may be determined whether conditions are met for determination of humidity via use of an exhaust gas oxygen sensor (e.g. UEGO), or other oxygen sensor, where such an estimate may be determined via alternating between applying first and second voltages to the exhaust gas sensor, and generating an indication of humidity based on sensor outputs at the first and second voltages, described above with regard to FIG. 8. However, because the engine is indicated to be in operation at time t1, conditions are not indicated to be met for determining humidity via the exhaust gas oxygen sensor. Instead, a humidity determination may be conducted via an ultrasonic sensor, provided a suitable object may be identified such that an accurate measurement of humidity may be obtained.

Accordingly, proceeding to time t2, object detection may be initiated. For example, object detection may include the use of one or more vehicle camera(s) (e.g. 186) in order to identify suitable objects for subsequently determining humidity. In other examples, if the vehicle is not equipped with one or more camera(s), then as an alternative the ultrasonic sensor(s) themselves may be used to identify potential suitable objects for conducting a humidity measurement.

As discussed above, object detection may include the one or more camera(s) capturing images, and storing the images at the controller (e.g. 12), for example. Such images may be processed via object recognition algorithms stored at the controller, in order to identify suitable objects for conducting a humidity measurement. For example, suitable objects may include objects that are stationary with respect to the vehicle, objects above a predetermined threshold size, objects with a predetermined shape, objects with an indicated lack of surface roughness, objects with a preferred angle of orientation, etc.

Between time t2 and time t3, it may be understood that, via the use of one or more camera(s), a suitable object for conducting a humidity measurement is identified. Responsive to identification of a suitable object, it may be further determined as to the objects position with respect to the vehicle, such that an optimally positioned ultrasonic sensor may be utilized to conduct the humidity measurement. For example, as discussed above, camera sensor(s) (e.g. 187) may be used to indicate an approximate location of the object with respect to the vehicle, and the controller may process the information in order to select an optimally positioned ultrasonic sensor to utilize for the humidity measurement. More specifically, the selected ultrasonic sensor may be selected based on the object, identified by one of the cameras, being within a transmission path of the selected sensor. As such, it may be understood that between time t2 and t3, a suitable object was detected, and an optimally positioned ultrasonic sensor was selected for conducting a humidity determination measurement. As the engine is operating, and a suitable object was identified for conducting the relative humidity measurement, it may be understood that the suitable object may likely be another vehicle traveling at essentially the same speed and direction as the vehicle conducting the humidity measurement. As such, it may be understood that conducting a humidity measurement via ultrasonic sensors may be accomplished while the vehicle is in operation (e.g. being propelled via an engine or an onboard energy storage device).

Between time t2 and t3, after a suitable object has been identified, and an optimal ultrasonic sensor selected, a humidity measurement may be conducted. For the sake of brevity, the method of conducting the humidity measurement will not be reiterated in full detail here.

However, it may be understood that the humidity measurement may be conducted according to the methods depicted above with regard to FIGS. 4-6. Briefly, determining humidity may comprise transmitting a plurality of signals from a single sensor, each at a different frequency, receiving reflected signals of the transmitted signals, determining attenuation values only for each of the reflected signals which have the same transit time from transmission to receipt, determining differences between pairs of the attenuation values, and converting the differences to an indication of relative humidity.

Accordingly, at time t3, it is indicated that humidity has been determined. More specifically, humidity may be accurately determined to be the value of humidity indicated by plot 1430 at time t3. With humidity determined, certain vehicle parameters may be adjusted accordingly, as discussed in detail above with regard to FIG. 9. In this example illustrative timeline 1400, only one vehicle operating parameter (EGR) is illustrated, for clarity. As illustrated, because humidity is indicated to have increased, EGR may be reduced, in order to avoid lean engine operation due to the increase humidity. Accordingly, between time t3 and t4, EGR is reduced according to the latest humidity measurement. Furthermore, while not explicitly shown, it may be understood that the most recent humidity measurement may be stored at the controller. Still further, while not explicitly illustrated, one or more additional vehicle operating parameters may be adjusted responsive to the humidity measurement. For example, as discussed above, an amount of spark advance or retard, a borderline spark value, a fuel octane estimate, etc., may be adjusted.

At time t4, the vehicle engine is turned off. In this example timeline, the engine shutoff may be understood to include a deceleration fuel shutoff event (DFSO). However, while the engine is off, it may be understood that an intake and exhaust valve may be maintained activated on at least one cylinder, such that the engine may cycle air through the intake manifold to the exhaust manifold.

At time t5, humidity determination conditions are again met, indicated by plot 1405. Because the engine is off due to a DFSO event, an exhaust gas oxygen sensor (e.g. UEGO) may be utilized to determine humidity. In other words, such an event may comprise an opportunity to preferentially conduct a humidity measurement via the exhaust gas oxygen sensor over conducting a humidity measurement via an ultrasonic sensor. A method for determining humidity via the use of an exhaust gas oxygen sensor is detailed above with regard to the method depicted in FIG. 9. Thus, an in-depth description of how a humidity detection may be accomplished via an exhaust gas oxygen sensor will not be reiterated here. However, it may be understood that, between time t5 and t6, a humidity determination (humidity indication) may be conducted via the exhaust gas oxygen sensors. Accordingly, at time t6, it is indicated that a new ambient humidity measurement has been determined, indicated by plot 1420. As such, the vehicle controller may update a previous humidity indication with the recent selected humidity indication.

The ambient humidity determination may be stored at the controller, such that vehicle operational parameters may be adjusted according to the new humidity determination. As the engine remains off from time t6 to t7, no adjustments are made to the amount of EGR provided to the engine (e.g. none in this case as the engine is off). However, at time t7, the engine is again activated, and thus an amount of EGR provided to the engine is adjusted accordingly, based on the most recent humidity determination measurement. In other words, the amount of EGR is adjusted based on the humidity determined at time t6, and which was stored at the controller.

Between time t7 and t8, the vehicle operates via the engine, with vehicle parameters being adjusted according to the most recent humidity measurement conducted via the exhaust gas oxygen sensor while the engine was deactivated (e.g. spun unfueled with at least one cylinder maintaining intake and exhaust valve function).

Turning now to FIG. 15, an example timeline 1500 is depicted illustrating how a distance threshold between an object of interest and a vehicle exhaust may be adjusted responsive to an indication of ambient humidity. Timeline 1500 includes plot 1505, indicating whether conditions are met for regeneration of a diesel particulate filter (DPF), over time. Timeline 1500 further includes plot 1510, indicating a vehicle velocity, over time. Line 1511 represents a threshold velocity, above which a DPF regeneration may be conducted without taking into determining a position of a potential object with respect to an exhaust of the vehicle. However, below the threshold velocity, an object within a threshold distance of the exhaust may result in the DPF regeneration procedure being aborted, or postponed.

Accordingly, timeline 1500 further includes plot 1515, indicating whether an object is detected as being positioned near the vehicle exhaust, over time. Timeline 1500 further includes plot 1520, indicating whether a humidity measurement has been obtained, over time, and where it may be understood that "no" means that a humidity measurement has not been conducted since a previous humidity estimation, and where "yes" indicates a current humidity measurement has been conducted. Timeline 1500 further includes plot 1525, indicating a position of an object with respect to the vehicle exhaust, over time. In this example illustration "−" may refer to decreasing distance between an object and the vehicle exhaust, whereas "+" may refer to increasing distance between the object and the vehicle exhaust. Line 1526 refers to a first distance threshold, and line 1527 refers to an adjusted, second threshold, where the thresholds may be adjusted based on an indication of ambient humidity, for example, discussed above and which will be discussed further below. Timeline 1500 further includes plot 1530, indicating whether DPF regeneration is taking place "yes", or not "no". Furthermore, timeline 1500 further includes plot 1535, indicating humidity, and plot 1540, indicating ambient temperature, over time. For plot 1540, a "+" indicates increasing (e.g. higher) temperature, while a "−" indicates decreasing (e.g. lower) temperature.

At time t0, it may be understood that the vehicle is in operation, and traveling at a low velocity, indicated by plot 1510. In some examples, such a low velocity may be indicative of a vehicle that is stopped, or substantially stopped. DPF regeneration conditions are not indicated to be met, illustrated by plot 1505. Accordingly, a potential object of interest is not as of yet detected, illustrated by plot 1515, and thus object position is not indicated. As DPF regeneration conditions are not met, a DPF regeneration procedure is not in progress, illustrated by plot 1530. Actual humidity is near 100%, indicated by plot 1535, and furthermore, a humidity determination procedure has not been conducted since a last time a humidity determination procedure was conducted, illustrated by plot 1520.

At time t1, DPF regeneration conditions are indicated to be met, illustrated by plot 1505. As discussed above, DPF regeneration conditions may be met responsive to a threshold pressure difference across the DPF being reached, as indicated by one pressure sensor (e.g. 80) positioned upstream of the DPF, and another pressure sensor (e.g. 82) positioned downstream of the DPF. Other examples may include a threshold number of miles driven since a previous DPF regeneration procedure, or a threshold duration of engine operation being reached since a previous DPF regeneration procedure.

Responsive to a DPF regeneration request, it may be determined whether the vehicle is traveling above a threshold velocity. The threshold velocity in this example timeline is illustrated by line 1511. If the vehicle is indicated to be traveling above the threshold velocity, then a DPF regeneration event may be conducted without first determining whether there is an object or objects close to the vehicle exhaust, as air flow due to the vehicle traveling velocity may serve to cool and disperse exhaust gas such that objects near the exhaust do not pose a concern. However, in this example timeline, the vehicle is indicated to be traveling substantially below the threshold velocity. Accordingly, the controller may initiate a search for objects of interest positioned close to the vehicle exhaust. As discussed above, such a search may include the controller commanding one or more onboard camera(s) (e.g. 186) to capture images in the proximity of the vehicle exhaust, and process the images using suitable object detection algorithms, in order to indicate whether potential objects of interest are positioned close to the exhaust. In other examples, if a vehicle is not equipped with one or more camera(s), such a search may include using one or more ultrasonic sensor(s) (e.g. 185) to detect objects near the exhaust.

In this example timeline, it may be understood that at time t1, with DPF regeneration conditions being met, and the vehicle being indicated to be below the threshold velocity, one or more onboard camera(s) may be commanded via the controller to search for objects positioned near the exhaust. Accordingly, at time t2, potential objects are detected, indicated by plot 1515. Furthermore, during the search via the use of one or more onboard camera(s), it may be understood that it was determined that the potential object may be a suitable object for conducting an ambient humidity determination. Thus, a humidity determination procedure may be executed, as described in detail above with regard to FIGS. 4-6. As discussed above, conducting an ambient humidity determination may additionally rely on a determination of ambient temperature. More specifically, in such an example where a DPF regeneration procedure may be conducted, it may be desirable to measure ambient temperature as close as possible (e.g. near to) the vehicle exhaust, as temperature near the vehicle exhaust may be substantially greater than a temperature further away from the vehicle, due to engine operation. Furthermore, such an increased temperature may affect a localized humidity in a vicinity close to the vehicle exhaust, which may thus enable an adjustment of a distance threshold for enabling a DPF regeneration procedure. More specifically, an area of interest when conducting a DPF regeneration procedure may encompass an area between a vehicle exhaust and an object of interest, where that area may experience elevated temperatures which may thus affect a localized humidity in that area. Localized humidity differences may thus further affect a thermal conductivity of the air in that specified area, as discussed above with regard to FIGS. 10-11, and therefore determining temperature and humidity specific to that area may enable adjustment of a distance threshold for enabling a DPF regeneration procedure.

At time t3, it is indicated that a humidity determination procedure has been completed and that an ambient humidity has been determined. As discussed above and with regard to FIGS. 10-11, depending on percent humidity, thermal conductivity of air may vary. As such, knowledge of ambient temperature may enable adjustment of a distance threshold for conducting, or not conducting, a DPF regeneration procedure. Accordingly at time t3, a distance threshold may be adjusted. More specifically, a distance threshold may be set at a first threshold level, indicated by line 1526. In such an example, if an object is positioned closer to the exhaust than the threshold, then a DPF regeneration event may not be conducted (e.g. may be prevented from being conducted), and may be postponed. However, if an object were positioned at a greater distance from the exhaust than the threshold, then a DPF regeneration procedure may be conducted. In this example timeline, based on determined humidity and temperature, where the temperature may correspond to a temperature substantially near the vicinity of the exhaust, and where humidity may correspond to a localized humidity in the vicinity of the exhaust (e.g. roughly between the exhaust and an object of interest), the distance threshold may be adjusted. More specifically, the distance threshold may be adjusted from the first threshold level, indicated by line 1526, to a second distance threshold level, indicated by plot 1527.

With the distance threshold adjusted at time t3, between time t3 and t4, a distance determination of the object of interest from the vehicle exhaust may be determined via the ultrasonic sensor (e.g. 185). To improve operational use of the ultrasonic sensor, a distance detection threshold may be adjusted based on the indicated humidity and temperature, as discussed above in detail with regard to step 1155 at FIG. 11, and with regard to step 1230 at FIG. 12. As such, a distance measurement may be conducted between time t3 and t4 via the use of the ultrasonic sensor, such that an object position may be determined at time t4. Because the distance threshold was adjusted to the second distance threshold, indicated by line 1527, and because the object is indicated to be positioned at a distance greater than the adjusted distance threshold, a DPF regeneration procedure may be conducted. Accordingly, at time t4, DPF regeneration is initiated, indicated by plot 1530.

As discussed above, regenerating the DPF may include adjusting engine operating parameters to increase DPF temperature. Examples may include operating a heater (e.g. 75) coupled to the DPF, or by raising a temperature of engine exhaust by operating rich, or by direct injection of fuel into exhaust gas.

Between time t4 and t5, regeneration of the DPF may be conducted. While not explicitly shown, it may be understood that during the DPF regeneration procedure, one or more of the onboard camera(s) and ultrasonic sensor(s) may be continued to be utilized in order to indicate whether an object has moved into an area below the adjusted threshold distance. In such a case where an object is indicated to be below the adjusted threshold distance, the regeneration event may be terminated, and may in some examples be postponed.

Furthermore, between time t4 and t5, while the DPF regeneration procedure is in progress, soot load may be monitored via, for example a pressure differential across the DPF. Responsive to the pressure differential decreasing to a predetermined threshold pressure differential, the DPF regeneration procedure may end. Accordingly, at time t5 it may be understood that the DPF has been regenerated. Accordingly, the DPF regeneration procedure is terminated, indicated by plot 1530, as DPF regeneration conditions are no longer met, indicated by plot 1505. Furthermore, object detection operations may cease, as it is no longer desired to indicate whether an object is positioned in a proximity close to the vehicle exhaust, indicated by plot 1515.

Between time t5 and t6, vehicle speed increases, as the vehicle resumes typical driving operation.

In this way, a relative humidity measurement may be obtained under conditions where a relative humidity measurement is requested, such as responsive to threshold changes in ambient temperature or ambient pressure, or responsive to a threshold time of engine operation exceeding an engine operation time threshold, or a distance of vehicle travel greater than a distance threshold. Based on vehicle operating conditions, selecting whether to utilize an ultrasonic sensor, or an oxygen sensor, to conduct the relative humidity measurement may enable robust and accurate measurements of humidity at times when humidity determination is requested by the vehicle controller, rather than waiting for opportune times.

The technical effect is to recognize that an ultrasonic sensor may be utilized during fueled engine operation to conduct a relative humidity estimation whether the vehicle is moving or parked, and that in the case of non-fueled engine operation, an oxygen sensor may be better suited to conduct the humidity estimation. Thus, by selecting which method to use to determine relative humidity at a time when a request for relative humidity is triggered, a humidity estimation may be rapidly and accurately achieved. A further technical effect includes recognizing that relative humidity estimations during fueled engine operation and while the vehicle is traveling may only be conducted responsive to detection of a suitable object that is stationary with respect to the vehicle. In this way, via the use of onboard cameras, suitable objects may be identified, and an optimal ultrasonic sensor may be selected for conducting the humidity estimation based on a transmission path of the ultrasonic sensor at least partially overlapping the detected object.

The systems described herein, and with regard to FIGS. 1-2 and FIG. 8, along with the methods described herein and with regard to FIGS. 4-7, FIG. 9, and FIGS. 11-12, may enable one or more systems, and one or more methods. In one example, a method comprises indicating relative humidity from differences between pairs of reflected signals from a single ultrasonic sensor coupled to a vehicle, each of the reflected signals having substantially equivalent transit time from an object back to the ultrasonic sensor; indicating relative humidity from one or more sensors coupled to the vehicle other than the ultrasonic sensor; and selecting which relative humidity indication method to use in response to environmental or vehicle operating conditions. In a first example of the method, the method further comprises detecting exhaust gas constituents from a gas sensor coupled to an exhaust of an engine which propels the vehicle; and during non-fueled operation of the engine, indicating relative humidity from the gas sensor. A second example of the method optionally includes the first example and further includes wherein the selecting of which relative humidity indicating method to use comprises selecting the indicating of relative humidity from the gas sensor. A third example of the method optionally includes any one or more or each of the first and second examples and further comprises detecting the presence of an object from one or both of: the ultrasonic sensor positioned on the vehicle, and one or more onboard cameras. A fourth example of the method optionally includes any one or more or each of the first through third examples and further includes wherein the object is indicated to be stationary with respect to the vehicle, whether the vehicle is moving or is parked. A fifth example of the method optionally includes any one or more or each of the first through fourth examples and further includes wherein indicating relative humidity from differences between pairs of reflected signals from a single ultrasonic sensor further comprises: determining an attenuation value for each of the reflected signals; determining a difference in attenuation between each of the pairs of reflected signals; and converting the difference in attenuation to the indication of relative humidity via the use of a transfer function. A sixth example of the method optionally includes any one or more or each of the first through fifth examples and further includes wherein indicating relative humidity from differences between pairs of reflected signals from a single ultrasonic sensor further comprises: indicating an ambient temperature via an outdoor ambient temperature sensor. A seventh example of the method optionally includes any one or more or each of the first through sixth examples and further comprises updating a previous humidity indication with the selected humidity indication. An eighth example of the method optionally includes any one or more or each of the first through seventh examples and further includes wherein indicating relative humidity from differences between pairs of reflected signals or from one or more sensors coupled to the vehicle other than the ultrasonic sensor further includes one or more of the following: indicating relative humidity responsive to an indicated change in ambient temperature greater than an ambient temperature threshold, a change in ambient pressure greater than an ambient pressure threshold, a threshold time of engine operation exceeding an engine operation time threshold, and a distance of vehicle travel greater than a distance threshold.

Another example of a method comprises indicating relative humidity from differences between pairs of reflected signals from a single ultrasonic sensor coupled to a vehicle, each of the reflected signals having substantially equivalent transit time from an object back to the ultrasonic sensor; indicating relative humidity from one or more sensors coupled to the vehicle other than the ultrasonic sensor; selecting which relative humidity indication method to use in response to environmental or vehicle operating conditions; and adjusting vehicle operating conditions responsive to the selected relative humidity indication. In a first example of the method, the method further includes wherein indicating relative humidity from differences between pairs of reflected signals from a single ultrasonic sensor includes identifying an object of interest that is stationary with respect to the vehicle, and wherein the object of interest is within a transmission path of the single ultrasonic sensor. A second example of the method optionally includes the first example and further comprises selecting the ultrasonic sensor to use for indicating relative humidity from a plurality of ultrasonic sensors positioned at various locations on the vehicle. A third example of the method optionally includes any one or more or each of the first and second examples and further includes wherein the selecting the ultrasonic sensor to use is accomplished via one or more onboard cameras detecting the object within the transmission path of the ultrasonic sensor. A fourth example of the method optionally includes any one or more or each of the first through third examples and further includes wherein indicating relative humidity via the single ultrasonic sensor includes determining an attenuation value for each of the reflected signals, determining a difference in attenuation between each of the pairs of reflected signals, and converting the difference in attenuation to the indication of relative humidity via the use of a transfer function; and wherein indicating relative humidity via one or more sensors coupled to the vehicle other than the ultrasonic sensor includes detecting exhaust gas constituents from a gas sensor coupled to an exhaust of an engine which propels the vehicle, and indicating relative humidity from the gas sensor during non-fueled operation of the engine. A fifth example of the method optionally includes any one or more or each of the first through fourth examples and further comprises propelling the vehicle at least in part by the engine, where the engine includes an intake manifold and an exhaust manifold, and where the engine operates by combustion of fuel provided to the engine; controlling an amount of exhaust gas recirculated to the intake manifold of the engine while the engine is operating; and wherein adjusting vehicle operating conditions responsive to indicating relative humidity includes one of at least an amount of the exhaust gas recirculation, and an amount by which ignition timing of spark provided to the fuel for combustion is retarded or advanced. A sixth example of the method optionally includes any one or more or each of the first through fifth examples and further includes wherein the vehicle is a hybrid vehicle that can operate for extended time periods without operation of the engine. A seventh example of the method optionally includes any one or more or each of the first through sixth examples and further comprises regenerating a particulate filter coupled to the exhaust manifold and connected to an underbody of the motor vehicle by causing burning of particulate stored in the particulate filter resulting in hot gases exiting a rear of the motor vehicle; and wherein selecting which relative humidity indication method to use includes selecting the indicating relative humidity from differences between pairs of reflected signals from the single ultrasonic sensor, where the ultrasonic sensor is further selected from the plurality of ultrasonic sensors based on the selected ultrasonic sensor having a transmission path overlapping at least a portion of the hot gases exiting the rear of the motor vehicle.

A system for a vehicle comprises one or more ultrasonic sensors positioned at various points on the vehicle; a combustion engine configured with a plurality of cylinders, each having a plurality of intake and exhaust valves; an exhaust manifold removably coupled to the plurality of cylinders via the plurality of exhaust valves; an exhaust gas oxygen sensor positioned in the exhaust manifold; and a controller storing instructions in non-transitory memory, that when executed, cause the controller to: in a first condition, indicate relative humidity from differences between pairs of reflected ultrasonic signals from a single ultrasonic sensor, where each of the reflected signals are determined to have a substantially equivalent transit time from an object back to the ultrasonic sensor; in a second condition, indicate relative humidity via the exhaust gas oxygen sensor; and wherein the first condition includes an engine-on condition where the engine is combusting fuel, and wherein the second condition includes an engine-on non-fueling condition where the engine is not combusting fuel but where at least one pair of intake and exhaust valves are functioning to draw air through at least one cylinder. In a first example, the system further comprises an outside air temperature sensor; a barometric pressure sensor; and wherein the controller further stores instructions in non-transitory memory, that when executed, cause the controller to: trigger a request for the relative humidity indication responsive to one or more of a change in air temperature greater than an air temperature threshold since a previous relative humidity indication, and a change in air pressure greater than an air pressure threshold since the previous relative humidity measurement. A second example of the system optionally includes the first example, and further comprises one or more cameras positioned at various points on the vehicle and configured to obtain images proximal to the vehicle; and wherein the controller further stores instructions in non-transitory memory, that when executed, cause the controller to: in the first condition, detect the presence of an object from the one or more camera(s); indicate the presence of an object that is stationary with respect to the vehicle; and select the single ultrasonic sensor based on a transmission path of the single ultrasonic sensor overlapping with the stationary object.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, 1-4, 1-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:
1. A method comprising:
indicating relative humidity from differences between pairs of reflected signals from a single ultrasonic sensor coupled to a vehicle, each of the reflected signals having substantially equivalent transit time from an object back to the single ultrasonic sensor;

detecting exhaust gas constituents from a gas sensor coupled to an exhaust of an engine which propels the vehicle;
indicating relative humidity from the gas sensor during non-fueled operation of the engine; and
selecting which relative humidity indication method to use in response to environmental or vehicle operating conditions.

2. The method of claim 1, wherein the selecting of which relative humidity indicating method to use comprises selecting the indicating of relative humidity from the gas sensor.

3. The method of claim 1, further comprising detecting a presence of an object from one or both of: the single ultrasonic sensor coupled to the vehicle, and one or more onboard cameras.

4. The method of claim 3, wherein the object is indicated to be stationary with respect to the vehicle, whether the vehicle is moving or is parked.

5. The method of claim 3, wherein indicating relative humidity from differences between pairs of reflected signals from the single ultrasonic sensor further comprises:
determining an attenuation value for each of the reflected signals;
determining a difference in attenuation between each of the pairs of reflected signals; and
converting the difference in attenuation to the indication of relative humidity via the use of a transfer function.

6. The method of claim 5, wherein indicating relative humidity from differences between pairs of reflected signals from the single ultrasonic sensor further comprises:
indicating an ambient temperature via an outdoor ambient temperature sensor.

7. The method of claim 1, further comprising updating a previous humidity indication with the selected relative humidity indication.

8. The method of claim 1, wherein indicating relative humidity from differences between pairs of reflected signals or from the gas sensor further includes one or more of the following:
indicating relative humidity responsive to an indicated change in ambient temperature greater than an ambient temperature threshold, a change in ambient pressure greater than an ambient pressure threshold, a threshold time of engine operation exceeding an engine operation time threshold, and a distance of vehicle travel greater than a distance threshold.

9. A method comprising:
identifying an object that is stationary with respect to a vehicle, and wherein the object is within a transmission path of a single ultrasonic sensor coupled to the vehicle;
selecting the single ultrasonic sensor to use for indicating relative humidity from a plurality of ultrasonic sensors positioned at various locations on the vehicle responsive to one or more onboard cameras detecting the object within the transmission path of the single ultrasonic sensor;
indicating relative humidity from differences between pairs of reflected signals from the single ultrasonic sensor, each of the reflected signals having substantially equivalent transit time from the object back to the single ultrasonic sensor;
indicating relative humidity from one or more sensors coupled to the vehicle other than the single ultrasonic sensor;
selecting which relative humidity indication method to use in response to environmental or vehicle operating conditions; and
adjusting vehicle operating conditions responsive to the selected relative humidity indication.

10. The method of claim 9, wherein indicating relative humidity via the single ultrasonic sensor includes determining an attenuation value for each of the reflected signals, determining a difference in attenuation between each of the pairs of reflected signals, and converting the difference in attenuation to the indication of relative humidity via the use of a transfer function; and
wherein indicating relative humidity via the one or more sensors coupled to the vehicle other than the single ultrasonic sensor includes detecting exhaust gas constituents from a gas sensor coupled to an exhaust of an engine which propels the vehicle, and indicating relative humidity from the gas sensor during non-fueled operation of the engine.

11. The method of claim 10, further comprising:
propelling the vehicle at least in part by the engine, where the engine includes an intake manifold and an exhaust manifold, and where the engine operates by combustion of fuel provided to the engine;
controlling an amount of exhaust gas recirculated to the intake manifold of the engine while the engine is operating; and
wherein adjusting vehicle operating conditions responsive to indicating relative humidity includes adjusting one of at least an amount of the exhaust gas recirculation, and an amount by which ignition timing of spark provided to the fuel for combustion is retarded or advanced.

12. The method of claim 11, further comprising:
regenerating a particulate filter coupled to the exhaust manifold and connected to an underbody of the vehicle by causing burning of particulates stored in the particulate filter resulting in gases exiting a rear of the vehicle; and
wherein selecting which relative humidity indication method to use includes selecting the indicating relative humidity from differences between pairs of reflected signals from the single ultrasonic sensor, where the single ultrasonic sensor is further selected from the plurality of ultrasonic sensors based on the selected single ultrasonic sensor having a transmission path overlapping at least a portion of the gases exiting the rear of the vehicle.

13. The method of claim 10, wherein the vehicle is a hybrid vehicle that can operate without operation of the engine.

14. A system for a vehicle, comprising:
one or more ultrasonic sensors positioned at various points on the vehicle;
a combustion engine configured with a plurality of cylinders, each having a plurality of intake and exhaust valves;
an exhaust manifold removably coupled to the plurality of cylinders via the plurality of exhaust valves;
an exhaust gas oxygen sensor positioned in the exhaust manifold; and
a controller storing instructions in non-transitory memory, that when executed, cause the controller to:
in a first condition, indicate relative humidity from differences between pairs of reflected ultrasonic signals from a single ultrasonic sensor, where each of the reflected signals are determined to have a substantially equivalent transit time from an object back to the single ultrasonic sensor;

in a second condition, indicate relative humidity via the exhaust gas oxygen sensor; and wherein the first condition includes an engine-on condition where the is combusting fuel, and wherein the second condition includes an engine-on non-engine fueling condition where the engine is not combusting fuel but where at least one pair of intake and exhaust valves are functioning to draw air through at least one cylinder.

15. The system of claim 14, further comprising:

an outside air temperature sensor;

a barometric pressure sensor; and wherein the controller further stores instructions in non-transitory memory, that when executed, cause the controller to:

trigger a request for the relative humidity indication responsive to one or more of a change in air temperature greater than an air temperature threshold since a previous relative humidity indication, and a change in air pressure greater than an air pressure threshold since the previous relative humidity measurement.

16. The system of claim 14, further comprising;

one or more cameras positioned at various points on the vehicle and configured to obtain images proximal to the vehicle; and wherein the controller further stores instructions in non-transitory memory, that when executed, cause the controller to:

in the first condition, detect a presence of an object from the one or more camera(s);

indicate the presence of an object that is stationary with respect to the vehicle; and select the single ultrasonic sensor based on a transmission path of the single ultrasonic sensor overlapping with the stationary object.

* * * * *